(12) United States Patent
Takahashi et al.

(10) Patent No.: US 7,067,535 B2
(45) Date of Patent: Jun. 27, 2006

(54) 5-PHENYLBENZYLAMINE COMPOUNDS, PROCESS FOR THEIR PRODUCTION AND INTERMEDIATES FOR THEIR SYNTHESIS

(75) Inventors: Masami Takahashi, Osaka (JP); Tsutomu Miyake, Hyogo (JP); Hirokazu Yamakita, Osaka (JP); Akira Saito, Tokyo (JP); Hidetoshi Asai, Ibaraki (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 98 days.

(21) Appl. No.: 10/380,754

(22) PCT Filed: Sep. 26, 2001

(86) PCT No.: PCT/JP01/08338

§ 371 (c)(1),
(2), (4) Date: Mar. 19, 2003

(87) PCT Pub. No.: WO02/26710

PCT Pub. Date: Apr. 4, 2002

(65) Prior Publication Data
US 2004/0097548 A1    May 20, 2004

(30) Foreign Application Priority Data

Sep. 26, 2000   (JP) ............................. 2000-292264

(51) Int. Cl.
A61K 31/445 (2006.01)
C07D 211/26 (2006.01)
(52) U.S. Cl. ...................................... 514/329; 546/229
(58) Field of Classification Search ................ 546/229; 514/329
See application file for complete search history.

(56) References Cited

U.S. PATENT DOCUMENTS

| | | | |
|---|---|---|---|
| 5,576,317 A * | 11/1996 | Gonsalves | 514/231.2 |
| 5,686,615 A * | 11/1997 | Rosen | 546/185 |
| 5,990,125 A * | 11/1999 | Howard | 514/305 |
| 6,562,335 B1 * | 5/2003 | Piedimonte et al. | 424/93.2 |

FOREIGN PATENT DOCUMENTS

| | | |
|---|---|---|
| EP | 544488 A2 | 6/1993 |
| EP | 0 780 375 A1 | 6/1997 |
| EP | 1127861 A1 | 8/2001 |
| WO | WO 93/01170 A1 | 1/1993 |
| WO | WO 97/14671 A1 | 4/1997 |
| WO | WO 99/24423 A1 | 5/1999 |

OTHER PUBLICATIONS

Caplus DN 71: 449462, Kanakalakshmi et al Synthesis of some acetylbiphenyl derivatives and the Beckmann rearrangement of their oximes. Journal of the Indian Chemical Society (1969), 46(5), 444-50 CODEN: JICSAH; ISSN: 0019-4522; English.*
Cullmann, Frank, et al . Phytochemistry, vol. 45, No. 6, pp. 1235-1247, 1997.
Pavia, Michael R., Bioorganic & Medicinal Chemistry, vol. 4, No. 5, pp. 659-666, 1996.
Schmidt, Von Ulrich, et al. Agnew. Chem., vol. 101, No. 7, pp. 946-948, 1989.
Getahun, Zelleka, et al. Journal of Medical Chemistry, vol. 35, No. 6, pp. 1058-1067, 1992.
Plattner, Jacob J., et al. Journal of Medical Chemistry, vol. 28, No. 1, pp. 79-93, 1985.
Tamura, Yasumitsu, et al. Journal of Medical Chemistry, vol. 24, No. 8, pp. 1006-1101, 1981.
Ogiso, Akira, et al. Chem. Pahrm. Bull. vol. 22, No. 1, pp. 135-143, 1974.
Ogiso, Akira, et al. Chem. Pharm. Bull. vol. 22, No. 1, pp. 144-151, 1974.

(Continued)

Primary Examiner—Rita Desai
(74) Attorney, Agent, or Firm—Birch, Stewart, Kolasch & Birch, LLP

(57) ABSTRACT

The present invention relates to a 5-phenylbenzylamine compound represented by the formula [1]:

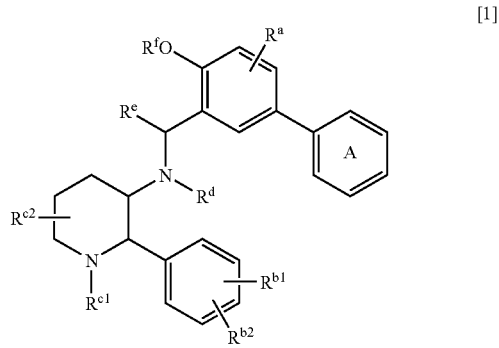

wherein Ring A represents a phenyl group having a substituent(s),
$R^a$, $R^{b1}$ and $R^{b2}$ each represent hydrogen atom, a halogen atom, a lower alkyl group, a halogeno-lower alkyl group or a lower alkoxy group,
$R^{c1}$ represents hydrogen atom, a lower alkyl group optionally substituted by a heterocyclic group, or an acyl group,
$R^{c2}$ and $R^e$ each represent hydrogen atom or a lower alkyl group,
$R^d$ represents hydrogen atom, a lower alkyl group or an acyl group, and
$R^f$ represents a lower alkyl group or a cyclic lower alkyl group,
or a pharmaceutically acceptable salt thereof, a process for preparing the same and synthetic intermediate thereof.

10 Claims, No Drawings

OTHER PUBLICATIONS

Sugimura, Yukio, et al. Tetrahedron Letters, No. 49, pp. 4985-4988, 1972.
Kanakalakshmi, B., et al. Jour. Indian Chem Soc., vol. 43, No. 7, pp. 469-472, 1966.
Mathai, K. P., et al. Jour. Indian Chem. Soc., vol. 40, No. 5, pp. 347-352, 1963.
Kanakalakshmi, B., et al. Jour. Indian Chem Soc., vol. 46, No. 5, pp. 444-450, 1969.
Hooper, J. W., et al. J. Chem. Soc. D, No. 2, pp. 111-112, 1971.
Chemical Abstracts, vol. 52, abstract No. 15527e, 1958.

* cited by examiner

5-PHENYLBENZYLAMINE COMPOUNDS, PROCESS FOR THEIR PRODUCTION AND INTERMEDIATES FOR THEIR SYNTHESIS

This application is the national phase under 35 U.S.C. § 371 of PCT International Application No. PCT/JP01/08338 which has an International filing date of Sep. 26, 2001, which designated the United States of America.

TECHNICAL FIELD

The present invention relates to a novel 5-phenylbenzylamine compound having excellent tachykinin receptor antagonistic action, a process for preparing the same and synthetic intermediate thereof.

BACKGROUND ART

Tachykinin is a general name for a group of neuropeptides, and there have been known substance P(SP), neurokinin-A, and neurokinin-B in mammals. These peptides are known to exhibit a various kinds of biological activities by binding their corresponding receptors which exist in vivo (neurokinin-1, neurokinin-2, neurokinin-3). Among them, SP is one of those which have the longest history in the neuropeptides, and have been studied in detail. Its existence was confirmed in an extract of horse intestinal tube in 1931, and it was a peptide comprising 11 amino acids, whose structure was determined in 1971.

SP exists widely in peripheral nervous system, and it has physiological activities such as vasodilation action, vascular permeability promoting action, smooth muscle contracting action, hypertarachia (neuronal excitement) action, salivation action, diuretic action, immunological action, etc., as well as a function of neurotransmitter of the primary sensory neuron. Specifically, it is known that SP released from the terminus of posterior horn of spinal cord upon pain impulse transfers pain information to the secondary neuron, and that SP released from the peripheral terminus induces an inflammatory reaction in the receptor. From these facts, SP is considered to be involved in various diseases (for example, pain, inflammation, allergy, thamuria, incontinence of urine, respiratory disease, mental illuness, depression, uneasiness, emesis, etc.), and also, SP is considered to be involved in Alzheimer type dementia (Review: Physiological Reviews, vol. 73, pp. 229–308 (published in 1993), Journal of Autonomic Pharmacology, vol. 13, pp. 23–93 (published in 1993)).

As a compound having a SP receptor antagonistic action, there are disclosed azabicyclo[2.2.1]heptan-3-amine derivative, etc. in Japanese Provisional Patent Publication No. Hei 6-107563, morpholine derivative, thiomorpholine derivative, etc. in Japanese Provisional Patent Publication No. Hei 6-172178, fluoroalkoxybenzylamine derivative, etc. in Japanese national publication of PCT application No. 6-506473, and spiro[benzo(c)thiophen-1(3H),4'-piperidin]-2-oxide derivative in Japanese Provisional Patent Publication No. Hei 11-43489.

Currently, as a therapeutic agent for the above-mentioned various diseases (especially for emesis, etc.), there have not been discovered yet any compound having an excellent tachykinin receptor antagonistic action (specifically, SP receptor antagonistic action), and at the same time, having sufficiently satisfying safety, sustainability (metabolism, dynamics in vivo) and absorption, etc. Therefore, a compound has been sought for which has a different chemical structure from those of the known tachykinin receptor antagonistic compounds, has an excellent tachykinin receptor antagonistic action, and has sufficiently satisfying clinical effect as the therapeutic agent.

Accordingly, an object of the present invention is to provide a novel compound having excellent tachykinin receptor antagonistic action, and having a clinically satisfying effect in terms of safety, sustainability (metabolism, dynamics in vivo), absorption, etc.

SUMMARY OF THE INVENTION

The present invention relates to a 5-phenylbenzylamine compound represented by the formula [1]:

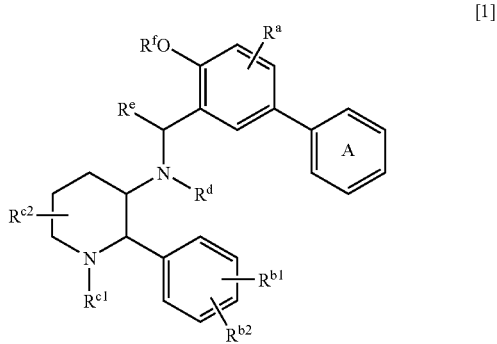

[1]

wherein Ring A represents a phenyl group having a substituent, $R^a$ represents hydrogen atom, a halogen atom, a lower alkyl group, a halogeno-lower alkyl group, or a lower alkoxy group, $R^{b1}$ represents hydrogen atom, a halogen atom, a lower alkyl group, a halogeno-lower alkyl group, or a lower alkoxy group, $R^{b2}$ represents hydrogen atom, a halogen atom, a lower alkyl group, a halogeno-lower alkyl group, or a lower alkoxy group, $R^{c1}$ represents hydrogen atom, a lower alkyl group optionally substituted by a heterocyclic group, or an acyl group, $R^{c2}$ represents hydrogen atom, or a lower alkyl group, $R^d$ represents hydrogen atom, a lower alkyl group, or an acyl group, $R^e$ represents hydrogen atom, or a lower alkyl group, and $R^f$ represents a lower alkyl group or a cyclic lower alkyl group, or a pharmaceutically acceptable salt thereof.

More specifically, it relates to a 5-phenylbenzylamine compound represented by the formula [1-a]:

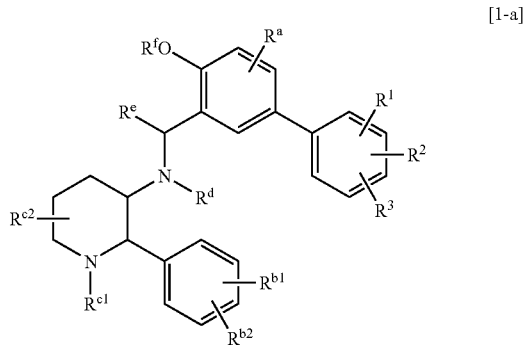

[1-a]

wherein R¹ represents a halogen atom, a lower alkyl group, a halogeno-lower alkyl group, a lower alkoxy group, a hydroxy-lower alkyl group, a lower alkoxy-lower alkyl group, an amino group optionally substituted by a lower alkyl group, phenyl group, naphthyl group, nitro group, cyano group, —CO—NH-lower alkyl, —CO—N(lower alkyl)₂, —NH—CO-lower alkyl, —COO-lower alkyl, or a heterocyclic group optionally substituted, R² represents hydrogen atom, a halogen atom, a lower alkyl group, a halogeno-lower alkyl group, a lower alkoxy group, or cyano group, R³ represents hydrogen atom, a halogen atom, a lower alkyl group, a halogeno-lower alkyl group, a lower alkoxy group, or cyano group, $R^a$, $R^{b1}$, $R^{b2}$, $R^{c1}$, $R^{c2}$, $R^d$, $R^e$ and $R^f$ have the same meanings as defined above, or a pharmaceutically acceptable salt thereof.

Also, the present invention relates to a process for preparing a 5-phenylbenzylamine compound represented by the formula [1]:

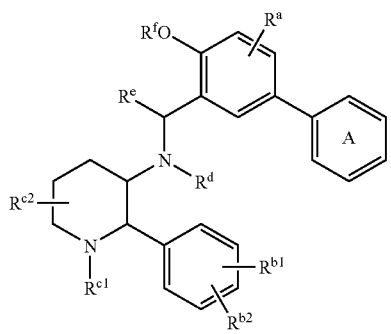

wherein Ring A, $R^a$, $R^{b1}$, $R^{b2}$, $R^{c1}$ $R^{c2}$, $R^d$, $R^e$ and $R^f$ have the same meanings as defined above, or a pharmaceutically acceptable salt thereof which comprises subjecting a compound represented by the formula [2]:

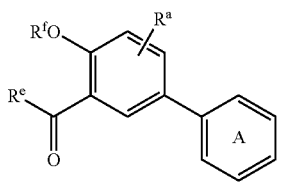

wherein Ring A, $R^a$, $R^e$ and $R^f$ have the same meanings as defined above, and a compound represented by the formula [3]:

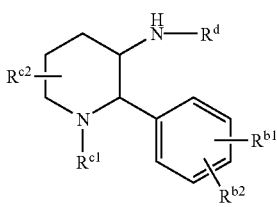

wherein $R^{b1}$, $R^{b2}$, $R^{c1}$, $R^{c2}$ and $R^d$ have the same meanings as defined above, or a salt thereof to reductive condensation reaction, and converting the product into a pharmaceutically acceptable salt thereof, if desired.

Moreover, the present invention relates to a compound represented by the formula [2]:

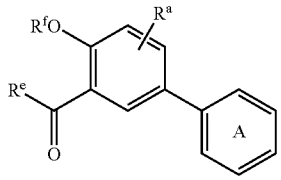

wherein Ring A, $R^a$, $R^e$ and $R^f$ have the same meanings as defined above.

The present invention also relates to a pharmaceutical composition comprising the above-mentioned compound in an effective dose for treatment and a pharmaceutically acceptable carrier.

The present invention further relates to the above-mentioned compound for use as a clinically effective ingredient.

The present invention further relates to use of the above-mentioned compound for preparing a medicament for prophylaxis or treatment of diseases selected from inflammation, allergic disease, pain, migraine, neuralgia, itchiness, cough, central nervous system disease, digestive organs disease, nausea, emesis, urinary disorder, circulatory disease and immune disorder.

The present invention further relates to a method for prophylaxis or treatment of diseases selected from inflammation, allergic disease, pain, migraine headache, neuralgia, itchiness, cough, central nervous system disease, digestive organs disease, nausea, emesis, urinary disorder, circulatory disease and immune disorder which comprises administering the above-mentioned compound in a clinically effective dose to a mammal.

BEST MODE FOR CARRYING OUT THE INVENTION

In the present invention, as Ring A in the compound [1], there may be mentioned a phenyl group having a substituent.

As $R^a$, there may be mentioned for example, hydrogen atom; a halogen atom such as fluorine atom, chlorine atom, etc.; a lower alkyl group such as methyl group, etc.; a halogeno-lower alkyl group such as trifluoromethyl group, etc.; or a lower alkoxy group such as methoxy group, etc.

As $R^{b1}$, there may be mentioned, for example, hydrogen atom; a halogen atom such as fluorine atom, chlorine atom, etc.; a lower alkyl group such as methyl group, etc.; a halogeno-lower alkyl group such as trifluoromethyl group, etc.; or a lower alkoxy group such as methoxy group, etc.

As $R^{b2}$, there may be mentioned, for example, hydrogen atom; a halogen atom such as fluorine atom, chlorine atom, etc.; a lower alkyl group such as methyl group, etc.; a halogeno-lower alkyl group such as trifluoromethyl group, etc.; or a lower alkoxy group such as methoxy group, etc.

As $R^{c1}$, there may be mentioned, for example, hydrogen atom; a lower alkyl group optionally substituted by a heterocyclic group such as triazolylmethyl group, etc.; or an acyl group represented by a lower alkanoyl group such as formyl group, acetyl group, etc.

As $R^{c2}$, there may be mentioned, for example, hydrogen atom; a lower alkyl group such as methyl group, etc.

As $R^d$, there may be mentioned, for example, hydrogen atom; a lower alkyl group such as methyl group, etc.; or an acyl group represented by a lower alkanoyl group such as formyl group, acetyl group, etc.

As $R^e$, there may be mentioned, for example, hydrogen atom; or a lower alkyl group such as methyl group, etc.

As $R^f$, there may be mentioned, for example, a lower alkyl group such as methyl group, ethyl group, propyl group, etc.; or a cyclic lower alkyl group such as cyclopropyl group, etc.

Among the compound [1] of the present invention, as the preferred compound, a compound [1-a] may be mentioned.

As $R^1$ in the compound [1-a], there may be mentioned, for example, a halogen atom such as fluorine atom, chlorine atom, etc.; a lower alkyl group such as methyl group, etc.; a halogeno-lower alkyl group such as trifluoromethyl group, etc.; a lower alkoxy group such as methoxy group, etc.; a hydroxy-lower alkyl group such as hydroxymethyl group, etc.; a lower alkoxy-lower alkyl group such as methoxymethyl group, etc.; an amino group optionally substituted by a lower alkyl group such as dimethylamino group, etc.; phenyl group; naphthyl group; nitro group; cyano group; a —CO—NH-lower alkyl such as methylcarbamoyl group, etc.; a —CO—N(lower alkyl)$_2$ such as dimethylcarbamoyl group, etc.; —NH—CO-lower alkyl such as methylcarbonylamino group, etc.; a —COO-lower alkyl such as methoxycarbonyl group; or a heterocyclic group optionally substituted such as a trifluoromethyltetrazolyl group, a triazolyl group, a thiazolyl group, a thiadiazolyl group, etc.

As $R^2$, there may be mentioned, for example, hydrogen atom; a halogen atom such as fluorine atom, chlorine atom, etc.; a lower alkyl group such as methyl group, etc.; a halogeno-lower alkyl group such as trifluoromethyl group, etc.; a lower alkoxy group such as methoxy group, etc.; or cyano group.

As $R^3$, there may be mentioned, for example, hydrogen atom; a halogen atom such as fluorine atom, chlorine atom, etc.; a lower alkyl group such as methyl group, etc.; a halogeno-lower alkyl group such as trifluoromethyl group, etc.; a lower alkoxy group such as methoxy group, etc.; or cyano group.

As $R^a$, $R^{b1}$, $R^{b2}$, $R^{c1}$, $R^{c2}$, $R^d$, $R^e$ and $R^f$ in the compound [1-a], those as mentioned above may be mentioned.

Among the objective compound [1-a] of the present invention, as a preferred compound, there may be mentioned a compound wherein $R^a$ is hydrogen atom or a lower alkoxy group, $R^{b1}$ is hydrogen atom or a halogen atom, $R^{b2}$ is hydrogen atom, $R^{c1}$ is hydrogen atom, $R^{c2}$ is hydrogen atom or methyl group, $R^d$ is hydrogen atom, $R^e$ is hydrogen atom, and $R^f$ is methyl group.

Among the objective compound [1-a] of the present invention, as a preferred combination of $R^1$, $R^2$ and $R^3$, there may be mentioned a compound wherein $R^1$ is a halogen atom, a lower alkyl group, a halogeno-lower alkyl group, a lower alkoxy group, a hydroxy-lower alkyl group or cyano group, $R^2$ is hydrogen atom, a halogen atom, a lower alkyl group or cyano group, and $R^3$ is hydrogen atom or a halogen atom.

As a more preferred compound, there may be mentioned a compound wherein $R^1$ is a halogen atom, a lower alkyl group, a halogeno-lower alkyl group or cyano group, $R^2$ is hydrogen atom, a halogen atom, a lower alkyl group or cyano group, and $R^3$ is hydrogen atom or a halogen atom.

Moreover, as a particularly preferred compound, there may be mentioned a compound wherein $R^1$ is a halogen atom or cyano group, R is hydrogen atom, a halogen atom or cyano group, and $R^3$ is hydrogen atom or a halogen atom.

Also, among the objective compound [1-a] of the present invention, a compound wherein $R^1$ is a substituent at 4-position is preferred.

Among the objective compound [1-a] of the present invention, as a preferred combination of $R^1$, $R^2$, $R^3$, $R^a$, $R^{b1}$, $R^{b2}$, $R^{c1}$, $R^{c2}$, $R^d$, $R^e$ and $R^f$, there may be mentioned a compound wherein $R^1$ is a halogen atom or cyano group, $R^2$ is hydrogen atom, a halogen atom or cyano group, $R^3$, $R^a$, $R^{b1}$, $R^{b2}$, $R^{c1}$, $R^d$, and $R^e$ are hydrogen atoms, $R^{c2}$ is hydrogen atom or methyl group, $R^f$ is methyl group, and $R^1$ is a substituent at 4-position.

Moreover, among the objective compound [1-a] of the present invention, preferred combinations of $R^1$, $R^2$, $R^3$, $R^a$, $R^{b1}$, $R^{b2}$, $R^{c1}$, $R^{c2}$, $R^d$, $R^e$ and $R^f$ are shown below.

(a) A compound wherein $R^1$ is a halogen atom, R is hydrogen atom, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is hydrogen atom, $R^d$ is hydrogen atom, $R^e$ is hydrogen atom and $R^f$ is methyl group.

(b) A compound wherein $R^1$ is a halogen atom, $R^2$ is a halogen atom, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is hydrogen atom, $R^d$ is hydrogen atom, $R^e$ is hydrogen atom and $R^f$ is methyl group.

(c) A compound wherein $R^1$ is a halogen atom, $R^2$ is a halogen atom, $R^3$ is a halogen atom, $R^a$ is hydrogen atom, $R^{b1}$ is hydrogen atom, $R^{b2}$ is hydrogen atom, $R^{c1}$ is hydrogen atom, $R^{c2}$ is hydrogen atom, $R^d$ is hydrogen atom, $R^e$ is hydrogen atom and $R^f$ is methyl group.

(d) A compound wherein $R^1$ is a halogen atom, $R^2$ is a lower alkyl group, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is hydrogen atom, $R^d$ is hydrogen atom, $R^e$ is hydrogen atom and $R^f$ is methyl group.

(e) A compound wherein $R^1$ is a halogen atom, $R^2$ is cyano group, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is hydrogen atom, $R^d$ is hydrogen atom, $R^e$ is hydrogen atom and $R^f$ is methyl group.

(f) A compound wherein $R^1$ is cyano group, $R^2$ is a halogen atom, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is hydrogen atom, $R^d$ is hydrogen atom, $R^e$ is hydrogen atom and $R^f$ is methyl group.

(g) A compound wherein $R^1$ is cyano group, $R^2$ is hydrogen atom, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is hydrogen atom, $R^d$ is hydrogen atom, $R^e$ is hydrogen atom and $R^f$ is methyl group.

(h) A compound wherein $R^1$ is a halogen atom, $R^2$ is hydrogen atom, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is methyl group, $R^d$ is hydrogen atom, $R^e$ is hydrogen atom, $R^f$ is methyl group.

(i) A compound wherein $R^1$ is a halogen atom, $R^2$ is a halogen atom, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is methyl group, $R^d$ is hydrogen atom, $R^e$ is hydrogen atom, $R^f$ is methyl group.

(j) A compound wherein $R^1$ is a halogen atom, $R^2$ is a halogen atom, $R^3$ is a halogen atom, $R^a$ is hydrogen atom, $R^{b1}$ is hydrogen atom, $R^{b2}$ is hydrogen atom, $R^{c1}$ is hydrogen atom, $R^{c2}$ is methyl group, $R^d$ is hydrogen atom, $R^e$ is hydrogen atom, $R^f$ is methyl group.

(k) A compound wherein $R^1$ is a halogen atom, $R^2$ is a lower alkyl group, $R^3$ is hydrogen atom, $R^a$ is hydrogen atom, $R^b$ is hydrogen atom, $R^{b2}$ is hydrogen atom, $R^{c1}$ is hydrogen atom, $R^{c2}$ is methyl group, $R^d$ is hydrogen atom, $R^e$ is hydrogen atom, $R^f$ is methyl group.

(l) A compound wherein $R^1$ is a halogen atom, $R^2$ is cyano group, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is methyl group, $R^d$ is hydrogen atom, $R^e$ is hydrogen atom, $R^f$ is methyl group.

(m) A compound wherein $R^1$ is cyano group, $R^2$ is a halogen atom, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is methyl group, $R^d$ is hydrogen atom, $R^e$ is hydrogen atom, $R^f$ is methyl group.

(n) A compound wherein $R^1$ is cyano group, $R^2$ is hydrogen atom, $R^3$ is hydrogen atom, $R^a$ is hydrogen atom, $R^{b1}$ is hydrogen atom, $R^{b2}$ is hydrogen atom, $R^{c1}$ is hydrogen atom, $R^{c2}$ is methyl group, $R^d$ is hydrogen atom, $R^e$ is hydrogen atom, $R^f$ is methyl group.

Moreover, among the compound [1-a] of the present invention, a preferred compound is shown by the formula [1-b]:

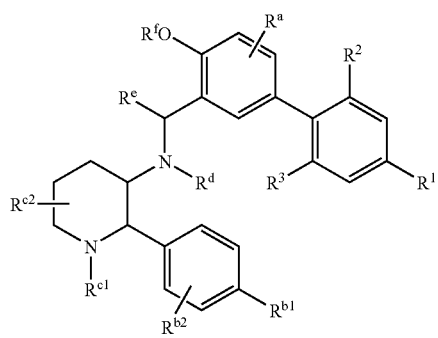

[1-b]

wherein $R^1$, $R^2$, $R^3$, $R^a$, $R^{b1}$, $R^{b2}$, $R^{c1}$, $R^{c2}$, $R^d$, $R^e$ and $R^f$ have the same meanings as defined above.

In the present invention, a compound in which the lower alkyl group is methyl group is preferred, and a compound in which the halogen atom is fluorine atom or chlorine atom is preferred.

In the present invention, particularly preferred compounds are shown in Table 1.

TABLE 1

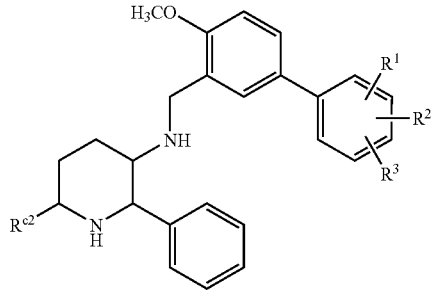

| | $R^1$ | $R^2$ | $R^3$ | $R^{c2}$ |
|---|---|---|---|---|
| (I) | 4-F | H | H | H |
| (II) | 4-Cl | H | H | H |
| (III) | 4-CN | H | H | H |
| (IV) | 4-F | 2-F | H | H |
| (V) | 4-F | 2-F | 6-F | H |
| (VI) | 4-F | 2-CH$_3$ | H | H |
| (VII) | 4-Cl | 2-CN | H | H |
| (VIII) | 4-CH$_3$ | 2-F | H | H |
| (IX) | 4-CN | 2-F | H | H |
| (X) | 4-CN | H | H | —CH$_3$ |
| (XI) | 4-CN | 2-F | H | —CH$_3$ |

In the present invention, particularly preferred compound is a compound selected from the following (A) to (F) or a pharmaceutically acceptable salt thereof.

(A) [2-methoxy-5-(4-fluorophenyl)benzyl][(2S,3S)-2-phenylpiperidin-3-yl]amine (B) [2-methoxy-5-(4-chlorophenyl)benzyl][(2S,3S)-2-phenylpiperidin-3-yl]amine (C) [2-methoxy-5-(4-cyanophenyl)benzyl][(2S,3S)-2-phenylpiperidin-3-yl]amine (D) [2-methoxy-5-(2-fluoro-4-cyanophenyl)benzyl][(2S,3S)$_2$-phenylpiperidin-3-yl]amine (E) [2-methoxy-5-(4-cyanophenyl)benzyl][(2S,3S,6R)$_6$-methyl-2-phenylpiperidin-3-yl]amine (F) [2-methoxy-5-(2-fluoro-4-cyanophenyl)benzyl]-[(2S,3S,6R)-6-methyl-2-phenylpiperidin-3-yl]amine The objective compound [1] of the present invention can be used for a pharmaceutical use either in a free form or in a form of a pharmaceutically acceptable salt. As the pharmaceutically acceptable salt of the compound [1], there may be mentioned, for example, an inorganic acid salt such as hydrochloride, sulfate, phosphate and hydrobromate, and an organic acid salt such as acetate, fumarate, oxalate, citrate, methanesulfonate, benzenesulfonate, tosylate, maleate, succinate and tartarate.

The objective compound [1] or a salt thereof according to the present invention includes any one of its internal salts, addition products, solvates and hydrates, etc.

Although an optical isomer based on an asymmetric carbon can be present in the objective compound [1] of the present invention, the present invention includes any of these optical isomers as well as mixtures thereof. Among these optical isomers, specifically preferred are those with (S,S) configuration.

Further, compounds to be included in the present invention are shown in Table 2.

TABLE 2

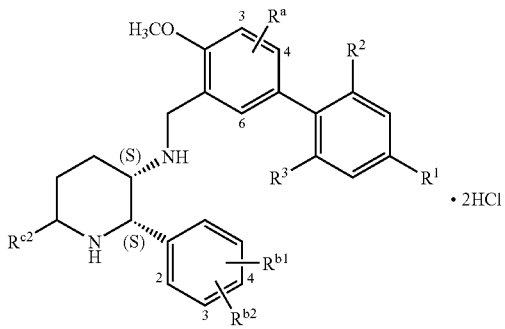

| Example | R¹ | R² | R³ | Rᵃ | Rᵇ¹ | Rᵇ² | Rᶜ² |
|---|---|---|---|---|---|---|---|
| 1 | 4-CON(CH₃)₂ | H | H | H | H | H | H |
| 2 | 4-CN | 2-Cl | H | H | H | H | H |
| 3 | 4-CN | 2-CH₃ | H | H | H | H | H |
| 4 | 4-CN | 2-CN | H | H | H | H | H |
| 5 | 4-CN | 2-OCH₃ | H | H | H | H | H |
| 6 | 4-F | 2-F | H | 6-OCH₃ | H | H | H |
| 7 | 4-F | 2-F | H | 4-Cl | H | H | H |
| 8 | 4-F | 2-F | H | 3-Cl | H | H | H |
| 9 | 4-F | 2-F | H | 6-CH₃ | H | H | H |
| 10 | 4-F | 2-F | H | 3-CH₃ | H | H | H |
| 11 | 4-F | 2-F | H | 4-CH₃ | H | H | H |
| 12 | 4-F | 2-F | H | H | 3-CH₃ | H | H |
| 13 | 4-F | 2-F | H | H | 2-F | H | H |
| 14 | 4-F | 2-F | H | H | 3-F | H | H |
| 15 | 4-F | 2-F | H | H | 4-F | 3-F | H |
| 16 | 4-F | 2-F | H | H | 4-F | 2-F | H |
| 17 | 4-F | 2-F | H | H | 4-F | 3-CH₃ | H |
| 18 | 4-F | 2-F | H | H | 2-Cl | H | H |
| 19 | 4-F | 2-F | H | H | 3-Cl | H | H |
| 20 | 4-F | 2-F | H | H | 4-Cl | H | H |
| 21 | 4-F | 2-F | H | H | 4-CF₃ | H | H |
| 22 | 4-F | 2-F | H | H | 4-OCH₃ | H | H |
| 23 | 4-Cl | H | H | H | H | H | —CH₃ |

The compound [1] or a pharmaceutically acceptable salt thereof of the present invention has an excellent tachykinin receptor antagonistic action, particularly an SP receptor antagonistic action, whereby it is useful as a safe medicament for prophylaxis and treatment for inflammation or allergic diseases (for example, atopic dermatitis, dermatitis, herpes, proriasis, asthma, bronchitis, expectoration, rhinitis, rheumatoid arthritis, osteoarthritis, osteoporosis, multiple sclerosis, conjunctivitis, ophthalmia, cystitis, etc.), pain, migraine, neuralgia, itchiness, cough, and further central nervous system diseases (for example, schizophrenia, Parkinson's disease, depression, uneasiness, psychosomatic disorder, morphine dependence, dementia(for example, Alzheimer's disease, etc.), etc.), digestive organs disease (for example, hypersensitive bowel disease, ulcerative colitis, Crohn's disease, disorder (for example, gastritis, gastric ulcer, etc.) related to urease-positive Spirillum (for example, helicobacter pylori, etc.), etc.), nausea, emesis, urinary disorder (for example, pollakiurea, urinary incontinence, etc.), circulatory disease (for example, angina pectoris, hypertension, cardiac failure, thrombosis, etc.) and immune disorder, etc. in mammals (for example, guinea pig, Mongolian gerbil, ferret, mouse, rat, hamster, rabbit, cat, dog, bovine, sheep, monkey, human, etc.).

In particular, the compound [1] or a pharmaceutically acceptable salt thereof of the present invention is characterized in that it is highly transportable into the brain, and therefore, it can last and act intracranially for a long period of time. It is less toxic showing almost no side effect, therefore it is safe, and it has a high pharmacological effect. Therefore, it is useful for a prophylactic and therapeutic agent for central nervous system diseases such as emesis, depression, etc., urinary disorder such as pollakiuria, etc.

The compound [1] or a pharmaceutically acceptable salt thereof of the present invention can be administered orally or parenterally, and it can be formulated into a suitable preparation, using a conventionally used pharmaceutical carrier for an oral or parental administration. As such a pharmaceutical carrier, there may be mentioned, for example, a binder (syrup, Gum Arabic, gelatin, sorbitol, tragacanth, polyvinylpyrrolidone, etc.), an excipient (lactose, sugar, corn starch, potassium phosphate, sorbitol, glycine, etc.), a lubricant (magnesium steareate, talc, polyethylene glycol, silica, etc.), a disintegrator (potato starch, etc.) and a wetting agent (anhydrous lauryl sodium sulfate, etc.), and the like.

Also, when these pharmaceutical preparations are administered orally, they may be a solid preparation such as tablets, granules, capsules, powders, or a liquid preparation such as solution, suspension, and emulsion. On the other hand, when they are administered parentally, for example, they can be administered as an injection solution or an infusion solution, using distilled water for injection, physiological saline, aqueous glucose solution, etc., or they may be administered as an inhalants or suppository, and the like.

A dose of the 5-phenylbenzylamine compound [1] or a pharmaceutically acceptable salt thereof of the present invention may vary depending on symptom of a patient, administration route, age or body weight of a patient, etc., and, for example, when it is administered to an adult patient suffering from emesis, depression or urinary disorder, it is preferably administered, in case of an injection, in a dose of usually about 0.01 to 10 mg/kg per day, particularly about 0.01 to 1 mg/kg per day, and in case of oral administration, it is preferably administered in a dose of usually about 0.01 to 20 mg/kg per day, particularly about 0.1 to 10 mg/kg or so per day, divided into 1 to 3 times.

According to the present invention, the objective compound [1] can be prepared by, for example, subjecting a compound represented by the formula [2]:

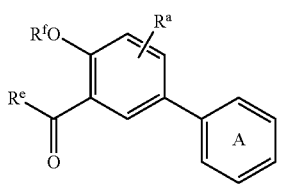

[2]

wherein Ring A, $R^a$, $R^e$ and $R^f$ have the same meanings as defined above, and a compound represented by the formula [3]:

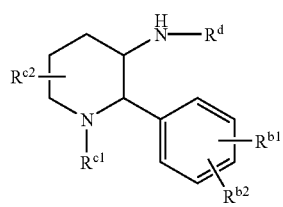

[3]

wherein $R^{b1}$, $R^{b2}$, $R^{c1}$, $R^{c2}$ and $R^d$ have the same meanings as defined above, or a salt thereof to reductive condensation reaction.

The reductive condensation reaction can be suitably carried out, for example, according to the method described in (a) Tetrahedron Letters, Vol. 31, p. 5595, 1990, (b) Journal of Organic Chemistry, Vol. 28, p. 3259, 1963, etc., in the presence of a reducing agent in a suitable solvent.

As the reducing agent, any agents may be used so long as it can be suitably used for a reductive amination. As such a reducing agent, there may be used a metal reducing agent, for example, a metal hydride (borane hydride (diborane, etc.), alane hydride), a metal hydride complex (lithium aluminum hydride, sodium borohydride, etc.), an organometal complex (borane-methylsulfide, 9-borabicyclononane (9-BBN), triethylsilane, sodium triacetoxyborohydride, sodium cyanoborohydride, etc.), etc. Moreover, if necessary, a Lewis acid (titanium tetrachloride, etc.) may be used as an additive.

Also, in the reductive condensation reaction, in place of using a reductive agent, it may be carried out under catalytic hydrogenation conditions. For example, by using a suitable catalyst such as a platinum catalyst, palladium-carbon, etc., it may be carried out in a suitable solvent under hydrogen atmosphere.

As a solvent, any solvents may be used so long as it does not exert any bad effect on the reaction. As such a solvent, there may be mentioned, for example, dimethylformamide, benzene, chlorinated hydrocarbon (dichloromethane, dichloroethane, etc.), ether (diethyl ether, tetrahydrofuran, dioxane, 1,2-dimethoxyethane, etc.), alcohol (methanol, ethanol, etc.), an organic acid (acetic acid, propionic acid, etc.), or a mixed solvent of the above-mentioned solvents, and the like.

Also, in the reductive condensation reaction, it is preferred to add an acid in a catalytic amount. As such an acid, there may be mentioned an organic acid such as formic acid, acetic acid, propionic acid, etc., and an inorganic acid such as hydrochloric acid, nitric acid, sulfuric acid, etc.

The present reaction can be suitably carried out under cooling to under heating, preferably from 0° C. to 100° C., more preferably in the range of 10° C. to 50° C.

The compound [1] thus obtained can be made a pharmaceutically acceptable salt by the conventional method, if desired.

The starting material [2] can be produced, for example, by the method A or the method B as mentioned below.

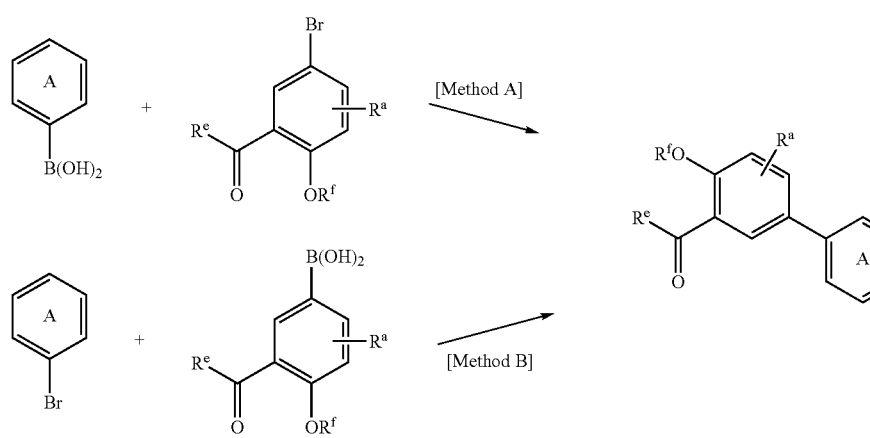

[2]

wherein Ring A, $R^a$, $R^e$ and $R^f$ have the same meanings as defined above.

The method A and the method B can be carried out according to the conventionally known methods such as Suzuki coupling reaction as disclosed in, for example, (a) Synthetic Communications, Vol. 11, p. 513, 1981, (b) Pure and Applied Chemistry, Vol. 57, p. 1749, 1985, (c) Chemical Reviews, Vol. 95, p. 2457, 1995, (d) Journal of Organic Chemistry, Vol. 57, p. 379, 1992, (e) Acta Chemica Scandinavica, Vol. 47, p. 221, 1993, etc. in a suitable solvent and in the presence of a base and a catalyst.

As the catalyst, a palladium catalyst (palladium acetate, palladium chloride, bistriphenylphosphine palladium chloride, tetrakis(triphenylphosphine) palladium, etc.), and the like can be suitably used. Also, when a divalent palladium catalyst having no ligand such as palladium acetate, palladium chloride, etc. is used, a phosphorus compound such as triphenylphosphine, tritollylphosphine, etc. is preferably added.

As the base, there may be suitably used an alkali metal carbonate such as sodium carbonate, potassium carbonate, etc., an alkali metal phosphoate such as sodium phosphoate, potassium phosphoate, etc., or an organic base such as triethylamine, diisopropylamine, etc.

As the solvent, any solvents may be used so long as it does not have any effect on the reaction, and there may be suitably used dimethylformamide, toluene, ethanol, methylene chloride, water or a mixture of the above-mentioned solvents.

The present reaction can be carried out under cooling to under heating, preferably at −20° C. to 180° C., more preferably in the range of 40° C. to 120° C.

Among the starting material [3], a compound wherein $R^{c2}$ is hydrogen atom can be produced, for example, by the method as described below.

[3]

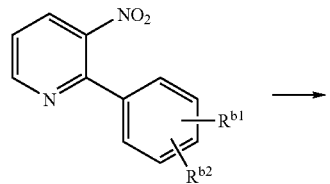

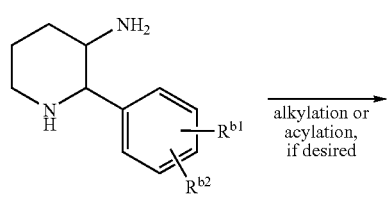

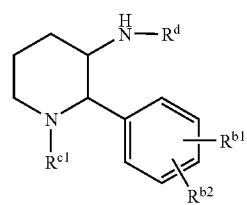

That is, a 2-phenyl-3-aminopyridine derivative is reduced to produce a 2-phenyl-3-aminopiperidine derivative, and then, the resulting compound is subjected to acylation or alkylation, if desired.

The reducing reaction can be carried out according to the method as described in Japanese national publication of PCT application No. 9-505275.

Alkylation or acylation can be carried out according to the conventional method, for example, in a suitably solvent (tetrahydrofuran, dichloromethane, etc.), in the presence of a base (triethylamine, pyridine, potassium carbonate, etc.), by reacting an alkylating agent (a lower alkyl halide, etc.) or an acylating agent (a lower alkanoyl halide, etc.) under cooling or under heating (preferably 0° C. to room temperature).

Also, among the starting material [3], a compound wherein $R^{c2}$ is hydrogen atom can be produced by the method as described below.

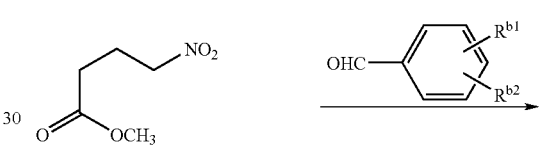

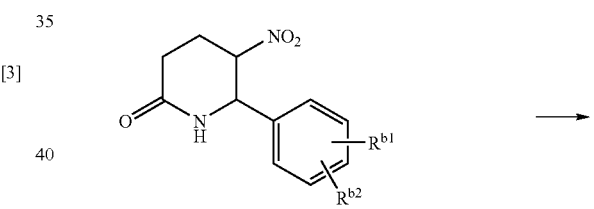

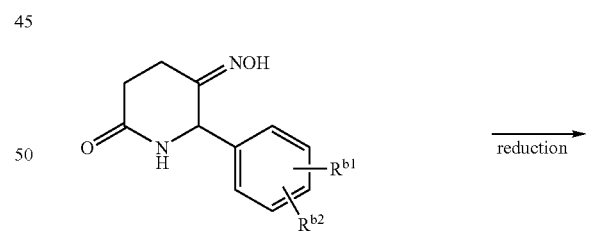

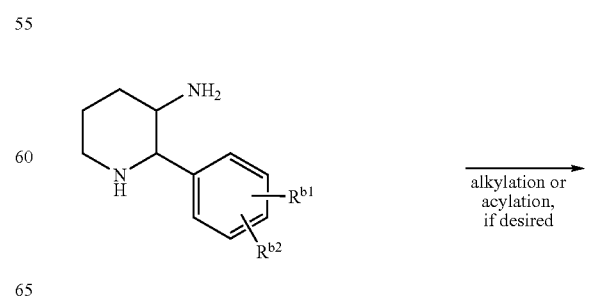

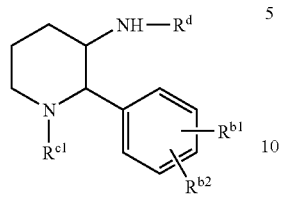

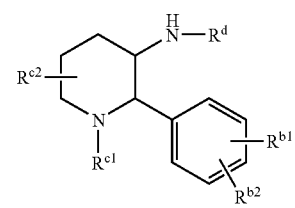

First, methyl 4-nitrobutyrate and a benzaldehyde derivative are reacted to produce a 5-nitro-6-phenyl-2-piperidinone derivative. Then, from the resulting compound, a piperidinedioneoxime derivative is produced. Moreover, oxime and a carbonyl group of the piperidinedioneoxime derivative are reduced to produce a 2-phenyl-3-aminopiperidine derivative, and further, the resulting derivative is, if desired, subjected to acylation or alkylation to produce the starting material [3].

The respective steps of producing a 2-phenyl-3-aminopiperidine derivative from methyl 4-nitrobutyrate can be suitably carried out by referring to Japanese Provisional Patent Publication No. 4-103570 or Japanese national publication of PCT application No. 6-508828. Moreover, acylation and alkylation can be carried out by the methods as mentioned above.

Also, among the starting material [3], a compound wherein $R^{c2}$ is a lower alkyl group can be produced, for example, by the method as described below.

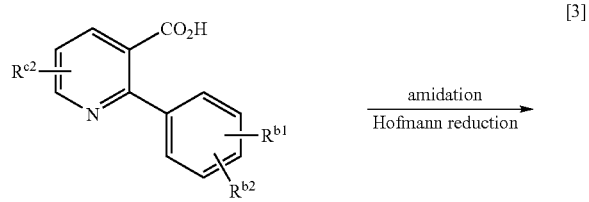

[3]

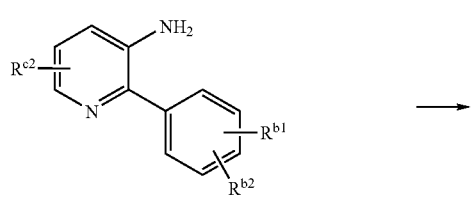

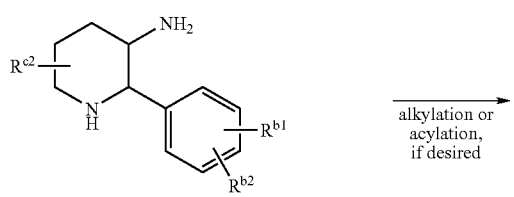

First, a carboxyl group of a 2-phenylnicotinic acid derivative is amidated and applied to Hofmann's reaction. Then, the resulting 2-phenyl-3-aminopyridine derivative is reduced to produce a 2-phenyl-3-aminopiperidine derivative, and further subjecting the resulting compound to acylation or alkylation, if desired.

Amidation of a carboxyl group of the 2-phenylnicotinic acid derivative and Hofmann's reaction can be carried out by the conventional method. For example, it can be carried out by the method as described in Japanese Provisional Patent Publication No. 4-103570 or Japanese national publication of PCT application No. 6-508828, or, the reaction may be carried out in t-butanol, by reacting diphenylphosphoryl azide, then, refluxing the mixture under heating and further treating with an acid.

Reduction can be carried out according to the method as described in Japanese national publication of PCT application No. 9-505275. Alkylation and acylation can be carried out by the methods as mentioned above.

In the present specification, the lower alkyl group means a straight or branched alkyl group having 1 to 6 carbon atoms such as methyl group, ethyl group, propyl group, butyl group, etc., preferably those having 1 to 4 carbon atoms. The lower alkoxy group means a straight or branched alkoxy group having 1 to 6 carbon atoms such as methoxy group, ethoxy group, propoxy group, butoxy group, etc., preferably those having 1 to 4 carbon atoms. The lower alkanoyl group means a straight or branched alkanoyl group having 1 to 6 carbon atoms such as formyl group, acetyl group, propionyl group, etc., preferably those having 1 to 4 carbon atoms. The cyclic lower alkyl group means a cycloalkyl group having 3 to 6 carbon atoms such as cyclopropyl group, cyclobutyl group, cyclopentyl group, cyclohexyl group, etc., preferably that having 3 carbon atoms.

EXAMPLE

In the following, the present invention will be explained in more detail by referring to Examples and Reference examples, but the present invention is not limited by these Examples.

Example 1

In 25 ml of methylene chloride were suspended 281 mg of (2S,3S)-2-phenylpiperidin-3-ylamine (2R,3R)-bis(4-methylbenzoyloxy)succinate, 115 mg of 2-methoxy-5-(4-fluorophenyl)benzaldehyde and 212 mg of sodium triacetoxyborohydride. This reaction mixture was stirred at room temperature under nitrogen atmosphere for 16 hours, and then, a saturated aqueous sodium hydrogen carbonate solution was added and the resulting mixture was extracted with chloroform. The organic layer was washed with brine, dried over anhydrous sodium sulfate and concentrated. The concentrated residue was purified by silica gel column chromatography (chloroform/methanol=10/1) to give a colorless oily product. This product was dissolved in ethyl acetate, and treated with an ethyl acetate solution containing 4N hydrochloric acid. Precipitated white crystal was collected by filtration, washed with ether and dried under reduced pressure to give 116 mg of [2-methoxy-5-(4-fluorophenyl)benzyl][(2S,3S)-2-phenylpiperidin-3-yl]amine dihydrochloride.

m.p.=277 to 279° C. (dec.)

Examples 2 to 100

In the same manner as in Example 1, the compounds shown in the following Tables 3 to 6 were obtained.

TABLE 3

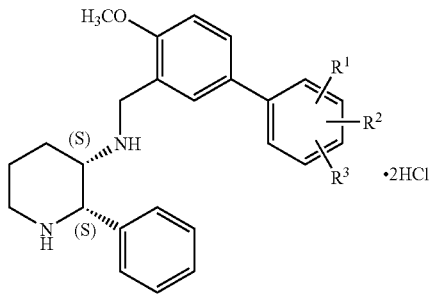

| Example | $R^1$ | $R^2$ | $R^3$ | Melting point |
|---|---|---|---|---|
| 2 | 2-$CH_3$ | H | H | 238–240° C. (dec.) |
| 3 | 3-$CH_3$ | H | H | 245–246° C. (dec.) |
| 4 | 4-$CH_3$ | H | H | 264–266° C. (dec.) |
| 5 | 2-Cl | H | H | 248–250° C. (dec.) |
| 6 | 3-Cl | H | H | 251–253° C. (dec.) |
| 7 | 4-Cl | H | H | 272–274° C. (dec.) |
| 8 | 2-F | H | H | 253–255° C. (dec.) |
| 9 | 3-F | H | H | 260–262° C. (dec.) |
| 10 | 2-$CON(CH_3)_2$ | H | H | 227–229° C. (dec.) |
| 11 | 4-$N(CH_3)_2$ | H | H | 126–127° C. (dec.) |
| 12 | 3-$OCH_3$ | H | H | 247–248° C. (dec.) |
| 13 | 4-$OCH_3$ | H | H | 260–261° C. (dec.) |
| 14 | 2-CN | H | H | 256–257° C. (dec.) |
| 15 | 3-CN | H | H | 267–268° C. (dec.) |
| 16 | 4-CN | H | H | 277–278° C. (dec.) |
| 17 | 2-$NO_2$ | H | H | 266–267° C. (dec.) |
| 18 | 4-$NO_2$ | H | H | 271–272° C. (dec.) |
| 19 | 2-$CO_2CH_3$ | H | H | 241–242° C. (dec.) |
| 20 | 4-$CO_2CH_3$ | H | H | 278–279° C. (dec.) |
| 21 | 2-$NHCOCH_3$ | H | H | 236–237° C. (dec.) |
| 22 | 2-$CH_2OH$ | H | H | 244–245° C. (dec.) |
| 23 | 4-$CH_2OH$ | H | H | 267–268° C. (dec.) |
| 24 | 2-$OCH_3$ | H | H | 218–220° C. (dec.) |
| 25 | 4-$CF_3$ | H | H | 274–275° C. (dec.) |
| 26 | 2-$CH_2OCH_3$ | H | H | 251–253° C. (dec.) |
| 27 | 4-Br | H | H | 275–277° C. (dec.) |
| 28 | 4-(5-$CF_3$-tetrazol-1-yl) | H | H | 260–261° C. (dec.) |
| 29 | 2-F | 6-F | H | 253–255° C. (dec.) |
| 30 | 4-F | 2-F | H | 270–271° C. (dec.) |
| 31 | 2-F | 3-F | H | 264–266° C. (dec.) |
| 32 | 2-F | 5-F | H | 264–265° C. (dec.) |
| 33 | 4-F | 3-F | H | 271–273° C. (dec.) |
| 34 | 3-F | 5-F | H | 267–268° C. (dec.) |
| 35 | 4-F | 3-F | 2-F | 276–277° C. (dec.) |
| 36 | 4-F | 3-F | 5-F | 269–270° C. (dec.) |
| 37 | 4-F | 2-F | 5-F | 267–268° C. (dec.) |
| 38 | 4-F | 2-F | 6-F | 275–277° C. (dec.) |

TABLE 3-continued

| Example | $R^1$ | $R^2$ | $R^3$ | Melting point |
|---|---|---|---|---|
| 39 | 4-F | 2-$CH_3$ | H | 274–275° C. (dec.) |
| 40 | 4-Cl | 2-F | H | 268–270° C. (dec.) |
| 41 | 4-Cl | 2-Cl | H | 269–270° C. (dec.) |
| 42 | 4-Cl | 2-$CH_3$ | H | 279–280° C. (dec.) |
| 43 | 4-Cl | 2-$NO_2$ | H | 264–266° C. (dec.) |
| 44 | 4-$CH_3$ | 2-F | H | 264–265° C. (dec.) |
| 45 | 4-$CF_3$ | 2-F | H | 254–255° C. (dec.) |
| 46 | 4-F | 2-$CH_2OH$ | H | 295–296° C. (dec.) |
| 47 | 4-Cl | 2-$CH_2OH$ | H | 291–293° C. (dec.) |
| 48 | 4-F | 2-$OCH_3$ | H | 242–244° C. (dec.) |
| 49 | 4-Cl | 2-CN | H | 267–268° C. (dec.) |
| 50 | 4-F | 2-CN | H | 270–271° C. (dec.) |
| 51 | 4-CN | 2-F | H | 280–281° C. (dec.) |

TABLE 4

| Example | $R^a$ | $R^{b1}$ | $R^{b2}$ | Melting point |
|---|---|---|---|---|
| 52 | 3-$OCH_3$ | H | H | 252–255° C. (dec.) |
| 53 | 4-$OCH_3$ | H | H | 259–263° C. (dec.) |
| 54 | 6-$OCH_3$ | H | H | >235° C. (dec.) |
| 55 | 3-Cl | H | H | 256–259° C. (dec.) |
| 56 | 4-Cl | H | H | 279–282° C. (dec.) |
| 57 | 3-$CH_3$ | H | H | >268° C. (dec.) |
| 58 | 4-$CH_3$ | H | H | 252–257° C. (dec.) |
| 59 | 6-$CH_3$ | H | H | 268–273° C. (dec.) |
| 60 | H | 2-$CH_3$ | H | 276–277° C. (dec.) |
| 61 | H | 3-$CH_3$ | H | 270–272° C. (dec.) |
| 62 | H | 4-$CH_3$ | H | 275–276° C. (dec.) |
| 63 | H | 2-F | H | 262–263° C. (dec.) |
| 64 | H | 3-F | H | 277–278° C. (dec.) |
| 65 | H | 4-F | H | 279–280° C. (dec.) |
| 66 | H | 4-F | 2-F | 265–267° C. (dec.) |
| 67 | H | 4-F | 3-F | 288–289° C. (dec.) |
| 68 | H | 4-F | 3-$CH_3$ | 279–281° C. (dec.) |
| 69 | H | 2-Cl | H | 248–250° C. (dec.) |
| 70 | H | 3-Cl | H | 285–287° C. (dec.) |

TABLE 4-continued

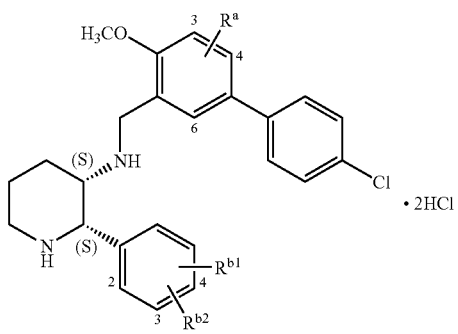

| Example | $R^a$ | $R^{b1}$ | $R^{b2}$ | Melting point |
|---|---|---|---|---|
| 71 | H | 4-Cl | H | 297–300° C. (dec.) |
| 72 | H | 4-CF$_3$ | H | 291–294° C. (dec.) |
| 73 | H | 4-OCH$_3$ | H | 265–268° C. (dec.) |

TABLE 5

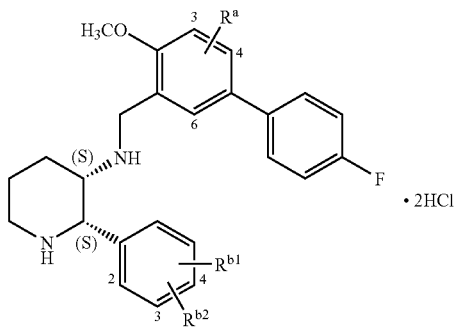

| Example | $R^a$ | $R^{b1}$ | $R^{b2}$ | Melting point |
|---|---|---|---|---|
| 74 | 3-OCH$_3$ | H | H | 259–262° C. (dec.) |
| 75 | 4-OCH$_3$ | H | H | 240–241° C. (dec.) |
| 76 | 6-OCH$_3$ | H | H | >227 ° C. (dec.) |
| 77 | 3-Cl | H | H | 260–262° C. (dec.) |
| 78 | 4-Cl | H | H | 275–279° C. (dec.) |
| 79 | 3-CH$_3$ | H | H | >262 ° C. (dec.) |
| 80 | 4-CH$_3$ | H | H | 261–264° C. (dec.) |
| 81 | 6-CH$_3$ | H | H | 256–258° C. (dec.) |
| 82 | H | 2-CH$_3$ | H | 261–262° C. (dec.) |
| 83 | H | 3-CH$_3$ | H | 268–269° C. (dec.) |
| 84 | H | 4-CH$_3$ | H | 281–283° C. (dec.) |
| 85 | H | 2-F | H | 245–246° C. (dec.) |
| 86 | H | 3-F | H | 276–277° C. (dec.) |
| 87 | H | 4-F | H | 289–291° C. (dec.) |
| 88 | H | 4-F | 2-F | 255–256° C. (dec.) |
| 89 | H | 4-F | 3-F | 286–287° C. (dec.) |
| 90 | H | 4-F | 3-CH$_3$ | 277–279° C. (dec.) |
| 91 | H | 2-Cl | H | 265–268° C. (dec.) |
| 92 | H | 3-Cl | H | 283–285° C. (dec.) |
| 93 | H | 4-Cl | H | 292–295° C. (dec.) |
| 94 | H | 4-CF$_3$ | H | 260–263° C. (dec.) |
| 95 | H | 4-OCH$_3$ | H | 286–288° C. (dec.) |

TABLE 6

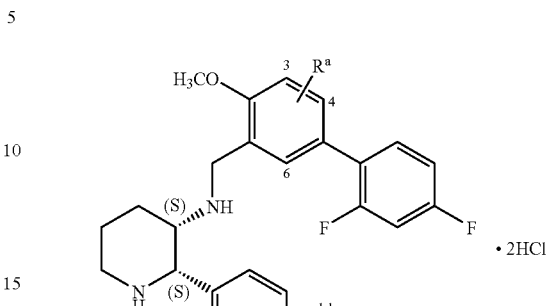

| Example | $R^a$ | $R^{b1}$ | $R^{b2}$ | Melting point |
|---|---|---|---|---|
| 96 | 3-OCH$_3$ | H | H | 267–268° C. (dec.) |
| 97 | 4-OCH$_3$ | H | H | 240–242° C. (dec.) |
| 98 | H | 2-CH$_3$ | H | 273–274° C. (dec.) |
| 99 | H | 4-CH$_3$ | H | 272–274° C. (dec.) |
| 100 | H | 4-F | H | 274–275° C. (dec.) |

Examples 101 to 102

In 25 ml of methylene chloride were dissolved 504 mg of (2S,3S)-2-phenylpiperidin-3-ylamine, 698 mg of 2-methoxy-5-(4-fluorophenyl)acetophenone and 1.2 ml of triethylamine. To the reaction mixture was added dropwise 1.43 ml of titanium tetrachloride solution (1.0 mol) in methylene chloride at 0° C. under nitrogen atmosphere. After stirring the mixture at room temperature for one hour, 8 ml of a methanol solution containing 539 mg of sodium cyanoborohydride was added dropwise to the mixture at 0° C. After stirring at room temperature for 30 minutes, 25 ml of 2N aqueous hydrochloric acid solution was added to the mixture. The aqueous layer was made alkaline with an aqueous potassium carbonate solution, and then, extracted with methylene chloride. The organic layer was washed with brine, dried over anhydrous sodium sulfate and concentrated. The concentrated residue was purified by silica gel column chromatography (chloroform/methanol=30/1) to give colorless oily products, [2-methoxy-5-(4-fluorophenyl)-(R)-α-methylbenzyl][(2S,3S)-2-phenylpiperidin-3-yl]amine and [2-methoxy-5-(4-fluorophenyl)-(S)-α-methylbenzyl][(2S,3S)-2-phenylpiperidin-3-yl]amine, were each obtained. They were each dissolved in ethyl acetate, and treated with an ethyl acetate solution containing 4N hydrochloric acid. Precipitated white crystals were collected by filtration, and further washed with ether, and dried under reduced pressure to give 76 mg of [2-methoxy-5-(4-fluorophenyl)-(R)-α-methylbenzyl][(2S,3S)-2-phenylpiperidin-3-yl]amine dihydrochloride and 21 mg of [2-methoxy-5-(4-fluorophenyl)-(S)-α-methylbenzyl][(2S,3S)-2-phenylpiperidin-3-yl]amine dihydrochloride.

TABLE 7

| Example | | Melting point |
|---|---|---|
| 101 | [2-Methoxy-5-(4-fluoro-phenyl)-(R)-α-methylbenzyl]-[(2S, 3S)-2-phenylpiperidin-3-yl]amine.dihydrochloride | 200–204° C. (dec.) |
| 102 | [2-Methoxy-5-(4-fluoro-phenyl)-(S)-α-methylbenzyl]-[(2S, 3S)-2-phenylpiperidin-3-yl]amine.dihydrochloride | 274–278° C. (dec.) |

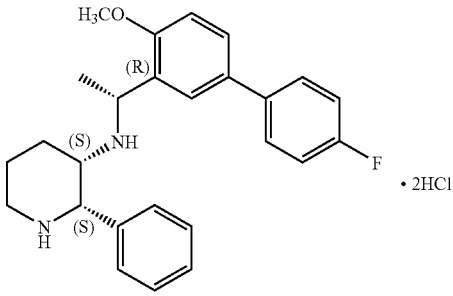

Example 103

(1) In 80 ml of chloroform was suspended (−)-di-p-toluoyl-L-tartarate of (2S,3S)-2-phenyl-3-aminopiperidine(4.0), and 40 ml of a saturated aqueous sodium bicarbonate solution was added to the suspension and dissolved under stirring. After the chloroform layer was washed with brine, the mixture was dried. The solvent was removed, 20 ml of chloroform was added to the residue, and the mixture was stirred under ice-cooling. To the mixture was added 1.5 g of di-t-butyldicarbonate, and the mixture was stirred under room temperature overnight. The solvent was removed, and the residue was purified by silica gel column chromatography (chloroform→chloroform/acetone=10/1) to give 1.40 g of (2S,3S)-2-phenyl-3-t-butyloxycarbonylaminopiperidine.

(2) A mixture comprising 300 mg of the compound obtained in (1), 300 mg of potassium carbonate, 222 mg of N-formyl-2-chloroacetamidehydrazone and 3 ml of dimethylformamide was stirred at 60° C. for 3 hours, and at 120° C. for 12 hours. The reaction mixture was poured into water, extracted with ethyl acetate, and after separating the liquids, the organic layer was successively washed with water and brine. The organic layer was dried and after removing the solvent, the residue was purified by silica gel column chromatography (chloroform/acetone=5/1) to give 161 mg of (2S,3S)-1-(1,2,4-triazol-3-ylmethyl)-2-phenyl-3-t-butyloxycarbonylaminopiperidine.

(3) In 5 ml of chloroform was dissolved 161 mg of the compound obtained in (2), and 1 ml of 4N hydrochloric acidethyl acetate was added to the solution and the resulting mixture was stirred overnight. After the reaction mixture was concentrated, a saturated aqueous sodium bicarbonate solution and chloroform were added to the residue, and the mixture was stirred. After separating the liquids, the organic layer was successively washed with water and brine. After drying the mixture, the solvent was removed. To 5 ml of a methylene chloride solution containing the residue, 124 mg of 2-methoxy-5-(4-fluorophenyl)benzaldehyde, and acetic acid (several drops) was added, under ice-cooling, 476 mg of sodium triacetoxyborohydride, and the resulting mixture was reacted under room temperature overnight. The reaction mixture was poured into a saturated aqueous sodium bicarbonate solution and the liquids were separated, the aqueous layer was extracted with methylene chloride. The whole organic layer was successively washed with water and brine, and after drying, the solvent was removed and the residue was purified by NH silica gel plate (chloroform/ethyl acetate=2/1) to give 61.5 mg of an objective compound in free form. This product was dissolved in 4 ml of chloroform, and 1 ml of 4N hydrochloric acid-ethyl acetate was added to the solution. After stirring the mixture for 10 minutes, the mixture was concentrated, and solidified by adding diethyl ether, and the solid was collected by filtration to give 51.2 mg of (2S,3S)-1-(1,2,4-triazol-3-ylmethyl)-2-phenyl-3-[[2-methoxy-5-(4-fluorophenyl)benzyl]amino]piperidine trihydrochloride.

m.p.=208–210° C. (dec.)

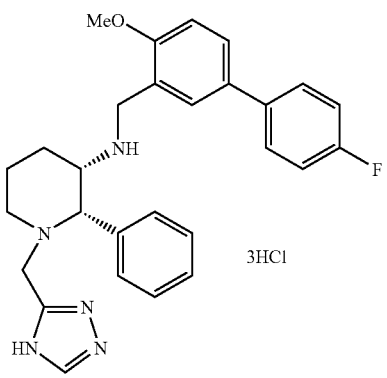

Example 104

A mixture comprising 220 mg of (2S,3S)-2-phenyl-3-t-butyloxycarbonylaminopiperidine obtained in Example 103 (1), 220 mg of potassium carbonate, 188.2 mg of N-carbomethoxy-2-chloroacetamidehydrazone and 2.1 ml of dimethylformamide was stirred at 70° C. for 12 hours, and at 140° C. for 2 hours. The reaction mixture was poured into water, extracted with ethyl acetate, and after separating the liquids, the organic layer was successively washed with water and brine, After drying the mixture, the solvent was removed. The residue was dissolved in 4 ml of chloroform, 1 ml of 4N hydrochloric acid-ethyl acetate was added to the solution and the resulting mixture was stirred overnight, and then concentrated. To the residue were added a saturated aqueous sodium bicarbonate solution and chloroform, and the resulting mixture was stirred, and after separating the liquids, the organic layer was successively washed with water and brine, and dried. By removing the solvent, an oily residue was obtained. To 5 ml of a methylene chloride solution containing the resulting product, 124 mg of 2-methoxy-5-(4-fluorophenyl)benzaldehyde and acetic acid (several drops) was added 476 mg of sodium triacetoxyborohydride under ice-cooling, and reacted under room temperature overnight. The reaction mixture was poured into a saturated aqueous sodium bicarbonate solution and the liquids were separated, and the aqueous layer was extracted with methylene chloride. The whole organic layer was successively washed with water and brine, and after drying the mixture, the solvent was removed. Then, the residue was purified by silica gel plate (chloroform/acetone=5/1) to give an objective compound in free form. This product was dissolved in 4 ml of chloroform, 1 ml of 4N hydrochloric acid-ethyl acetate was added to the solution and the resulting mixture was stirred for 10 minutes. Then, the mixture was concentrated, solidified by adding diethyl ether, and the solid was collected by filtration to give 10 mg of (2S,3S)-1-[5(4H)-oxo-1,2,4-triazol-3-yl]methyl-2-phenyl-3-[[2-methoxy-5-(4-fluorophenyl)benzyl]amino]piperidine dihydrochloride.

m.p.=198–200° C. (dec.)

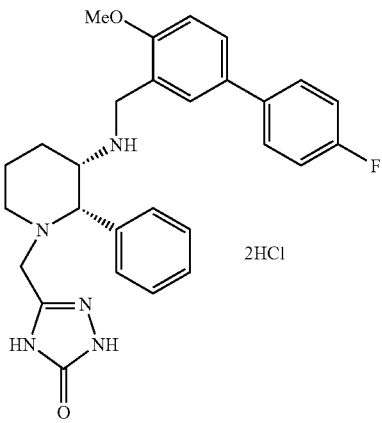

Example 105

(1) In 10 ml of dimethylformamide was dissolved 850 mg of (2S,3S)-2-phenyl-3-t-butyloxycarbonylaminopiperidine obtained in Example 103(1), under ice-cooling, 850 mg of potassium carbonate and 0.29 ml of methyl bromoacetate were added to the solution and the resulting mixture was stirred at 60° C. overnight. The reaction mixture was poured into water, extracted with ethyl acetate, and then, the liquids were separated. The organic layer was successively washed with water and brine, and after drying the mixture, the solvent was removed. The residue was purified by silica gel column chromatography (hexane/ethyl acetate=4/1) to give 1.02 g of (2S,3S)-1-methoxycarbonylmethyl-2-phenyl-3-t-butyloxycarbonylaminopiperidine.

(2) In 30 ml of chloroform was dissolved 1.02 g of the compound obtained in (1), and under ice-cooling, 10 ml of 4N hydrochloric acid-ethyl acetate was added to the solution dropwise. Under room temperature, the mixture was stirred for 30 minutes, the solvent was removed, and a saturated aqueous sodium bicarbonate solution and chloroform were added to the residue and the resulting mixture was stirred. After separating the liquids, the organic layer was successively washed with water and brine, and dried. By removing the solvent, a crude material of (2S,3S)-1-methoxycarbonylmethyl-2-phenyl-aminopiperidine was obtained and it was used in the next step without purification.

(3) To 10 ml of a methylene chloride solution containing 0.976 mmol of (2S,3S)-1-methoxycarbonylmethyl-2-phenylaminopiperidine obtained in (2), 270 mg of 2-methoxy-5-(4-fluorophenyl)benzaldehyde and acetic acid (several drops) was added 1.03 g of sodium triacetoxyborohydride under ice-cooling, and the mixture was reacted under room temperature overnight. The reaction mixture was poured into a saturated aqueous sodium bicarbonate solution and the liquids were separated. The aqueous layer was extracted with methylene chloride, and the whole organic layer was successively washed with water and brine. After drying, the solvent was removed to give 390 mg of (2S,3S)-1-methoxycarbonylmethyl-2-phenyl-3-[[2-methoxy-5-(4-fluorophenyl)benzyl]amino] piperidine.

(4) 390 mg of the compound obtained in (3) and 3 ml of hydrazine monohydrate were refluxed in 10 ml of ethanol, and then ethanol was removed and the residue was purified by NH silica gel column chromatography (chloroform/ethyl acetat=4/1) to give 330 mg of (2S,3S)-1-hydrazidecarbonylmethyl-2-phenyl-3-[[2-methoxy-5-(4-fluorophenyl)benzyl]amino]piperidine.

(5) To a solution of 150 mg of the compound obtained in (4) in mixture of 2 ml of conc. hydrochloric acid and 9 ml of water was added 315 mg of potassium thiocyanate, and the resulting mixture was refluxed for 3 hours. After cooling, sodium hydroxide was added until the pH of the mixture became 8 to 9, and the resulting mixture was extracted with ethyl acetate. After separating the liquids, the whole organic layer was successively washed with water and brine, and after drying the mixture, the solvent was removed. To the residue was added 2N aqueous sodium hydroxide solution and after refluxing for 12 hours, the reaction mixture was poured into water, and extracted with ethyl acetate. After separating the liquids, the organic layer was successively washed with water and brine, and after drying the mixture, the solvent was removed. The residue was purified by silica gel column chromatography (chloroform/ethyl acetate=4/1) to give an oily residue. This oily residue was dissolved in 4 ml of chloroform, 1 ml of 4N hydrochloric acid-ethyl acetate was added to the solution and the resulting mixture was stirred for 30 minutes. After concentrating the mixture, diethyl ether was added to the residue to solidify the product, and the solid was collected by filtration to obtain 9.0 mg of (2S,3S)-1-[5(4H)-thioxo-1,2,4-triazol-3-yl]methyl-2-phenyl-3-[[2-methoxy-5-(4-fluorophenyl)benzyl]amino]piperidinedihydrochloride.
m.p.=180–182° C. (dec.)

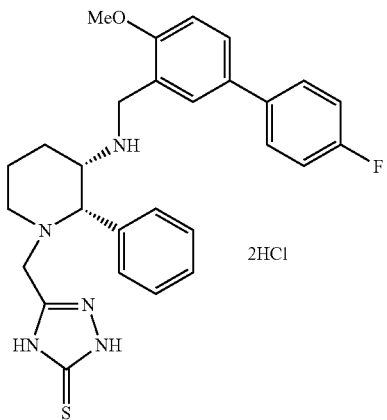

Example 106

To a tetrahydrofuran solution containing 100 mg of (2S,3S)-1-hydrazidecarbonylmethyl-2-phenyl-3-[[2-methoxy-5-(4-fluorophenyl)benzyl]amino]piperidine obtained in Example 105(4) was added 64 mg of triphosgene under ice-cooling, and the resulting mixture was stirred under room temperature overnight. The reaction mixture was poured into a saturated aqueous sodium bicarbonate solution and extracted with ethyl acetate. After separating the liquids, the organic layer was successively washed with water and brine, and after drying the mixture, the solvent was removed. The residue was purified by NH silica gel column chromatography (chloroform/methanol=4/1) to give an oily residue. This oily residue was dissolved in 4 ml of chloroform, and 1 ml of 4N hydrochloric acid-ethyl acetate was added to the solution and the resulting mixture was stirred for 30 minutes and concentrated. Diethyl ether was added to the residue to solidify the product and the product was collected by filtration to give 26.8 mg of (2S,3S)-1-[5(4H)-oxo-1,3,4-oxadiazol-2-yl]methyl-2-phenyl-3-[[2-methoxy-5-(4-fluorophenyl)benzyl]amino]piperidine-dihydrochloride.
m.p.=212–216° C. (dec.)

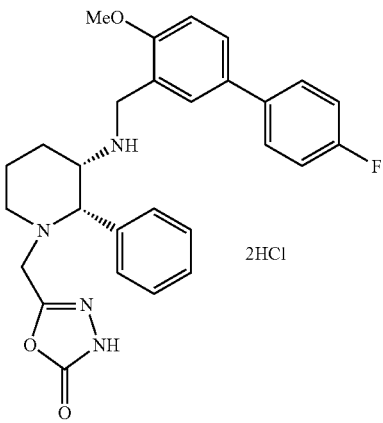

Example 107

In 10 ml of methylene chloride were suspended 176 mg of (±)-cis-2-phenylpiperidin-3-ylamine, 280 mg of 2-methoxy-5-(2-trifluoromethylphenyl)benzaldehyde, 424 mg of sodium triacetoxyborohydride and 0.2 ml of acetic acid. This reaction mixture was stirred at room temperature for 16 hours, a saturated aqueous sodium hydrogen carbonate solution was added to the mixture and the resulting mixture was extracted with chloroform. The organic layer was washed with brine, dried over anhydrous sodium sulfate and concentrated. The concentrated residue was purified by silica gel column chromatography (chloroform/methanol=10/1) to give a colorless oily product. This product was dissolved in ethyl acetate, and treated with an ethyl acetate solution of 4N hydrochloric acid. The precipitated white crystals were collected by filtration and washed with ethanol, and dried under reduced pressure to give 243 mg of [(±)-cis-2-phenylpiperidin-3-yl][2-methoxy-5-(2-trifluoromethylphenyl)benzyl]amine dihydrochloride.
m.p.=260–262° C.

Examples 108 to 110

In the same manner as in Example 107, the following compounds shown in Table 8 were obtained.

TABLE 8

[Structure: H3CO-substituted benzyl group attached to NH of a 2-phenylpiperidine, with biphenyl bearing R1, R2, R3 substituents; •2HCl]

| Example | R$^1$ | R$^2$ | R$^3$ | Melting point |
|---|---|---|---|---|
| 108 | 4-F | H | H | 272–273° C. |
| 109 | 2-CN | H | H | 281–282° C. |
| 110 | 3-CF$_3$ | 5-CF$_3$ | H | 248–250° C. |

Examples 111 to 113

(1) In 105 ml of N,N-dimethylformamide were dissolved 15 g of 2-chloro-6-methylnicotinic acid, 24.2 g of potassium carbonate and 25.3 g of methyl iodide, and the solution was stirred at room temperature for 16 hours. Thereafter, water and ethyl acetate were added to the mixture and the resulting liquids were separated. The aqueous layer was extracted with ethyl acetate again, the combined organic layers were successively washed with water and brine, dried and concentrated to give 16.1 g of a brownish oily product.

(2) To a mixed solvent comprising 260 ml of dioxane and 150 ml of aqueous 2N sodium carbonate solution were added the oily product obtained in (1), 10.6 g of phenylboric acid and 5.0 g of tetrakis(triphenylphosphine) palladium, and the mixture was refluxed under nitrogen flow and stirred for 16 hours. Thereafter, dioxane was removed under reduced pressure, water and ethyl acetate were added to the residue to effect extraction, and the liquids were separated. The aqueous layer was extracted with ethyl acetate again, the combined organic layers were successively washed with water and brine, dried and concentrated. To the concentrated residue were added 400 ml of methanol and 200 ml of aqueous 2N sodium hydroxide solution, and the mixture was refluxed for one hour. The reaction mixture was concentrated, water and methylene chloride were added to the residue and after removing black insoluble material by filtration, the liquids were separated. Salt was added to the aqueous layer and the mixture was extracted with chloroform again. The combined organic layers were dried over magnesium sulfate and concentrated to give 19.5 g of 2-phenyl-6-methylnicotinic acid.
m.p.=210–212° C.

(3) In 840 ml of t-butanol were dissolved 18.0 g of the compound obtained in (2) and 9.4 g of triethylamine. To the solution was added dropwise 25.6 g of diphenylphosphorylazide, and the resulting mixture was stirred at room temperature for one hour. Thereafter, the mixture was stirred for 16 hours while refluxing. After cooling the reaction mixture, t-butanol was removed under reduced pressure. The concentrated residue was purified by silica gel column chromatography. To the resulting compound were added 500 ml of ethanol and 50 ml of conc. hydrochloric acid. Moreover, 3.0 g of platinum oxide was added to the mixture, and the resulting mixture was stirred under 1 atm. Hydrogen atmosphere for 4 hours. After completion of stirring, 250 ml of water was added and the mixture was filtered through Celite. The filtrate was concentrated, and to the concentrated residue were added an aqueous sodium hydroxide solution and brine, and the resulting mixture was extracted with chloroform five times. The combined organic layers were dried and then concentrated. The concentrated residue was purified by silica gel column chromatography to give 2.0 g of (2SR, 3SR,6SR)-2-phenyl-6-methylpiperidin-3-yl-amine.
Oily Product (4) To a mixed solvent comprising 158 ml of ethanol and 5 ml of water were added 2.0 g of racemic compounds obtained in (3) and 4.06 g of (2R,3R)-bis(4-methylbenzoyloxy)succinate, and the mixture was stirred under heating. The reaction mixture was stirred while cooling to precipitate crystals. The crystals were collected by filtration, 90 ml of ethanol and 3.5 ml of water were again added to the crystals, while stirring under heating, to completely dissolve the crystals therein, and crystals were precipitated while cooling. This crystals were collected by filtration, washed with a small amount of ethanol, and then dried under vaccum to give 1.54 g of (2S,3S,6R)-2-phenyl-6-methylpiperidin-3-yl-amine (2R,3R)-bis(4-methylbenzoyloxy)succinate.
m.p.=180–182° C.

(5) The compound obtained in (4) was treated in the same manner as in Example 1 to give the compounds shown in the following Table 9.

TABLE 9

[Structure: H3CO-substituted benzyl attached to (S)-NH of a piperidine with (R)-H3C, (S) stereocenters, 2-phenyl and biphenyl bearing R1, R2, R3; •2HCl]

| Example | R$^1$ | R$^2$ | R$^3$ | Melting point |
|---|---|---|---|---|
| 111 | 4-Cl | H | H | 280–282° C. (dec.) |
| 112 | 4-CN | 2-F | H | 301–302° C. (dec.) |
| 113 | 4-CN | H | H | 298–300° C. (mp) |

Example 114

(1) In 100 ml of dimethylformamide was dissolved 10 g of 4-bromosalicyl aldehyde, the mixture was cooled by ice-bath, and 2.0 g of sodium hydride (60% in oil) was gradually added to the mixture and the resulting mixture was stirred for one hour. Thereafter, 10 ml of ethyl iodide was added to the mixture and the resulting mixture was stirred at room temperature for 5 hours. To the reaction mixture were added water, brine and ethyl acetate to effect extraction, and the liquids were separated. After the organic layer was dried, concentrated and the concentrated residue was recrystallized from hexane and ethyl acetate to give 7.8 g of 2-ethoxy-5-bromobenzaldehyde.
m.p.=70–71° C.
(2) 1.2 g of the compound obtained in (1) and 1.2 g of 4-chlorophenylboric acid were treated in the same manner as in Reference example 1 to give 1.16 g of 2-ethoxy-5-(4-chlorophenyl)benzaldehyde.
m.p.=88–90° C.
(3) The compound obtained in (2) and (2S,3S)-2-phenylpiperidin-3-ylamine (2R,3R)-bis(4-methylbenzoyloxy)succinate were treated in the same manner as in Example 1 to give the following compound.
m.p.=270–271° C. (dec.)

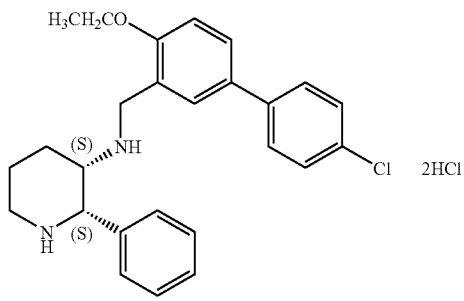

Example 115

(1) 1.2 g of the compound obtained in Example 114 (1) and 1.1 g of 4-cyanophenylboric acid were treated in the same manner as in Example 114(2) to give 0.73 g of 2-ethoxy-5-(4-cyanophenyl)benzaldehyde.
m.p.=110–121° C.
(2) In the same manner as in Example 114(3), the following compound was obtained.
m.p.=265–267° C. (dec.)

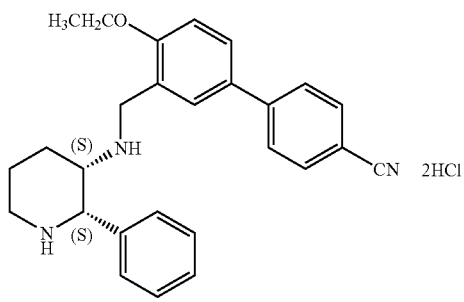

Example 116

(1) 10 g of 4-bromosalicyl aldehyde and 10 ml of propyl 2-iodide were treated in the same manner as in Example 114(1) to give 6.5 g of 2-(2-propoxy)-5-bromobenzaldehyde.
Oily Product
(2) 1.2 g of the compound obtained in (1) and 1.2 g of 4-chlorophenylboric acid were treated in the same manner as in Example 114(2) to give 0.36 g of 2-(2-propoxy)-5-(4-chlorophenyl)benzaldehyde.
Oily Product
(3) In the same manner as in Example 114(3), the following compound was obtained.
m.p.=274–276° C. (dec.)

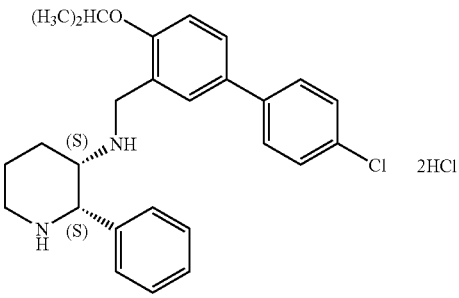

Example 117

(1) 1.2 g of the compound obtained in Example 116(1) and 1.1 g of 4-cyanoboric acid were treated in the same manner as in Example 114(2) to give 0.42 g of 2-(2-propoxy)-5-(4-cyanophenyl)benzaldehyde.
m.p.=94–96° C.
(2) In the same manner as in Example 114(3), the following compound was obtained.
m.p.=270–272° C. (dec.)

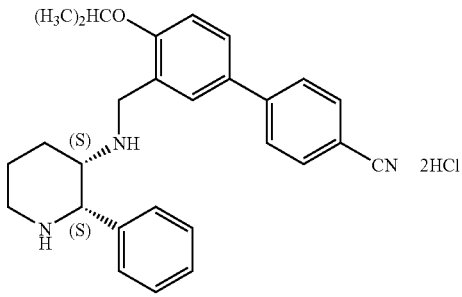

Reference Example 1

(1) To a solution in which 21.5 g of 2-methoxy-5-bromobenzaldehyde and 15.0 ml of trimethyl orthoformate were dissolved in 200 ml of methanol was added 3 g of strongly acidic ion exchange resin and the resulting mixture was stirred at room temperature. After one hour, the resin was removed by filtration, and the filtrate was made basic with a small amount of sodium methoxide and then concentrated. The concentrated residue was dissolved in 300 ml of tetrahydrofuran, and after cooling to −78° C., 69 ml of a hexane solution containing 1.6M n-butyl lithium was added dropwise to the mixture. After stirring for about 30 minutes, 56 ml of trimethoxy borane was added to the mixture at −78° C., and after elevating the temperature to 0° C., the mixture was stirred for one hour. Moreover, the mixture was stirred at room temperature for 2 hours, 100 ml of 2N aqueous hydrochloric acid solution was added to the mixture and the resulting mixture was stirred for 30 minutes. This mixture was made basic again with 2N aqueous sodium hydroxide solution, and then washed with ether. The aqueous layer was made acidic with 6N aqueous hydrochloric acid solution and extracted with chloroform. The organic layer was dried over anhydrous magnesium sulfate, concentrated and triturated with hexane to give 13.8 g of 3-formyl-4-methoxyphenylboric acid.

(2) To 1.9 g of the compound obtained in (1) were added 1.82 g of 2-bromobenzonitrile, 0.11 g of palladium acetate and 0.37 g of tri-o-tollylphosphine, and the mixture was suspended in 200 ml of toluene under nitrogen atmosphere. To the resulting mixture was added 11 ml of 2M aqueous sodium carbonate solution, and further a small amount of ethanol was added. The obtained solution was heated to 70° C. and stirred for 16 hours. The reaction mixture was cooled to room temperature, and formed black precipitate was removed by filtration. The filtrate was successively washed with an aqueous sodium bicarbonate solution and brine, dried over anhydrous magnesium sulfate, and then concentrated under reduced pressure. The concentrated residue was purified by silica gel column chromatography (n-hexane/chloroform/ethyl acetate=5/5/1), and crystallized from diisopropyl ether and n-hexane to give 1.13 g of 2-methoxy-5-(2-cyanophenyl)benzaldehyde.

m.p.=145–146° C.

Reference Examples 2 to 66

In the same manner as in Reference example 1, the compounds shown in the following Table 10 were obtained.

TABLE 10

| Reference example | $R^1$ | $R^2$ | $R^3$ | $R^a$ | Melting point |
|---|---|---|---|---|---|
| 2 | 4-F | H | H | H | 83–84° C. |
| 3 | 2-$CH_3$ | H | H | H | Oily product |
| 4 | 3-$CH_3$ | H | H | H | Oily product |
| 5 | 4-$CH_3$ | H | H | H | 73–74° C. |
| 6 | 2-Cl | H | H | H | 103–104° C. |
| 7 | 3-Cl | H | H | H | 105–106° C. |
| 8 | 4-Cl | H | H | H | 118–119° C. |
| 9 | 2-F | H | H | H | Oily product |
| 10 | 3-F | H | H | H | 81–82° C. |
| 11 | 2-$CON(CH_3)_2$ | H | H | H | 108–109° C. |
| 12 | 4-$N(CH_3)_2$ | H | H | H | 137–138° C. |
| 13 | 3-$OCH_3$ | H | H | H | Oily product |
| 14 | 4-$OCH_3$ | H | H | H | 124–125° C. |
| 15 | 3-CN | H | H | H | 116–117° C. |
| 16 | 4-CN | H | H | H | 148–150° C. |
| 17 | 2-$NO_2$ | H | H | H | 157–158° C. |
| 18 | 4-$NO_2$ | H | H | H | 134–135° C. |
| 19 | 2-$CO_2CH_3$ | H | H | H | 96–97° C. |
| 20 | 4-$CO_2CH_3$ | H | H | H | 146–147° C. |
| 21 | 2-$NHCOCH_3$ | H | H | H | 206–208° C. |
| 22 | 2-$CH_2OH$ | H | H | H | Oily product |
| 23 | 4-$CH_2OH$ | H | H | H | 130–131° C. |
| 24 | 2-$OCH_3$ | H | H | H | Oily product |
| 25 | 4-$CF_3$ | H | H | H | 156–157° C. |
| 26 | 2-$CH_2OCH_3$ | H | H | H | 75–76° C. |
| 27 | 4-Br | H | H | H | 146–147° C. |
| 28 | 2-F | 6-F | H | H | 130–131° C. |
| 29 | 4-F | 2-F | H | H | 112–113° C. |
| 30 | 2-F | 3-F | H | H | 118–120° C. |
| 31 | 2-F | 5-F | H | H | 103–104° C. |
| 32 | 4-F | 3-F | H | H | 74–75° C. |
| 33 | 3-F | 5-F | H | H | 113–114° C. |
| 34 | 4-F | 3-F | 2-F | H | 112–113° C. |
| 35 | 4-F | 3-F | 5-F | H | 111–113° C. |
| 36 | 4-F | 2-F | 5-F | H | 118–119° C. |
| 37 | 4-F | 2-F | 6-F | H | 148–149° C. |
| 38 | 4-F | 2-$CH_3$ | H | H | 93–94° C. |
| 39 | 4-Cl | 2-F | H | H | 152–154° C. |
| 40 | 4-Cl | 2-Cl | H | H | 162–163° C. |
| 41 | 4-Cl | 2-$CH_3$ | H | H | 90–91° C. |
| 42 | 4-Cl | 2-$NO_2$ | H | H | 176–177° C. |
| 43 | 4-$CH_3$ | 2-F | H | H | 108–109° C. |
| 44 | 4-$CF_3$ | 2-F | H | H | 120–121° C. |
| 45 | 4-F | 2-$CH_2OH$ | H | H | 51–53° C. |
| 46 | 4-Cl | 2-$CH_2OH$ | H | H | Oily product |
| 47 | 4-F | 2-$OCH_3$ | H | H | 110–111° C. |
| 48 | 4-Cl | H | H | 3-$OCH_3$ | 118–120° C. |
| 49 | 4-Cl | H | H | 4-$OCH_3$ | 134–136° C. |
| 50 | 4-Cl | H | H | 6-$OCH_3$ | 106–108° C. |
| 51 | 4-Cl | H | H | 3-Cl | 110–112° C. |
| 52 | 4-Cl | H | H | 4-Cl | 135–137° C. |
| 53 | 4-Cl | H | H | 3-$CH_3$ | 61–63° C. |
| 54 | 4-Cl | H | H | 4-$CH_3$ | 107–109° C. |
| 55 | 4-Cl | H | H | 6-$CH_3$ | 122–124° C. |
| 56 | 4-F | H | H | 3-$OCH_3$ | 114–118° C. |
| 57 | 4-F | H | H | 4-$OCH_3$ | 99–100° C. |
| 58 | 4-F | H | H | 6-$OCH_3$ | 81–83° C. |
| 59 | 4-F | H | H | 3-Cl | 90–92° C. |
| 60 | 4-F | H | H | 4-Cl | 134–136° C. |
| 61 | 4-F | H | H | 3-$CH_3$ | 60–62° C. |
| 62 | 4-F | H | H | 4-$CH_3$ | 81–83° C. |
| 63 | 4-F | H | H | 6-$CH_3$ | 93–95° C. |
| 64 | 4-F | 2-F | H | 3-$OCH_3$ | 106–109° C. |
| 65 | 4-F | 2-F | H | 4-$OCH_3$ | 138–139° C. |
| 66 | 3-$CF_3$ | 5-$CF_3$ | H | H | 160–161° C. |

Reference Example 67

(1) 42.0 g of trifluoroacetic acid anhydride was gradually added dropwise to a solution in which 34.4 g of 4-bromoaniline and 30 ml of triethylamine were dissolved in 600 ml of methylene chloride, under ice-cooling. After stirring the mixture under ice-cooling for one hour, the temperature of the mixture was elevated to room temperature, and the mixture was further stirred for one hour. The reaction mixture was concentrated, and crystallized from isopropyl ether and ethyl acetate to give 40.0 g of 4-bromo-trifluoroacetanilide.

m.p.=142–143° C.

(2) A solution in which 13.4 g of the compound obtained in (1) and 26.2 g of triphenylphosphine were dissolved in 200 ml of carbon tetrachloride was refluxed under heating for 16 hours. After cooling the mixture to room temperature, insoluble materials were removed by filtration, and the solvent was removed. The concentrated residue was dissolved in 100 ml of acetic acid, 13 g of sodium azide was added to the solution and the mixture was stirred at 70° C. for 3 hours. After completion of the reaction, water was added to the reaction mixture and the reaction mixture was extracted with chloroform. The organic layer was washed with a saturated aqueous sodium hydrogen carbonate solution, dried over anhydrous magnesium sulfate, and then concentrated. The concentrated residue was purified by silica gel column chromatography (chloroform) to give 7.23 g of 1-bromo-4-(5-trifluoromethyltetrazol-1-yl),benzene.
Oily Product (3) In the same manner as in Reference example 1(2) using 2.0 g of the compound obtained in (2), 0.96 g of 2-methoxy-5-[4-(5-trifluoromethyltetrazol-1-yl)phenyl]benzaldehyde was obtained. m.p.=186–187° C.

Reference Example 68

(1) In 60 ml of N,N-dimethylformamide were dissolved 6.2 g of 2-bromo-4-chlorophenol, 7.2 g of zinc cyanide and 3.5 g of tetrakis(triphenylphosphine) palladium, and the solution was stirred at 120° C. for 2 hours. The reaction mixture was cooled to room temperature, and the formed black precipitate was removed by filtration. After concentrating the filtrate, a saturated aqueous sodium hydrogen carbonate solution was added to the residue and the mixture was extracted with ethyl acetate. The organic layer was washed with water, dried over anhydrous magnesium sulfate, and concentrated under reduced pressure. The concentrated residue was purified by silica gel column chromatography (chloroform/ethyl acetate=10/1), and crystallized from n-hexane to give 2.7 g of 2-cyano-4-chlorophenol.
m.p.=166–168° C.

(2) To 5 ml of methylene chloride solution in which 460 mg of the compound obtained in (1) and 0.7 ml of triethylamine were dissolved was gradually added dropwise 0.84 ml of trifluoromethanesulfonic acid anhydride at −10° C. This solution was stirred at −10° C. for 30 minutes, water was added to the solution and the resulting mixture was extracted with chloroform. The organic layer was dried over anhydrous magnesium sulfate, and concentrated under reduced pressure. The concentrated residue was purified by silica gel column chromatography (n-hexane/ ethyl acetate=10/1). By using 0.55 g of the resulting oily product and 0.40 g of 3-formyl-4-methoxyphenylboric acid, the reaction was carried out in the same manner as in Reference example 1(2) to give 0.20 g of 2-methoxy-5-(2-cyano-4-chlorophenyl)benzaldehyde.
m.p.=187–189° C.

Reference Examples 69 to 70

In the same manner as in Reference example 68, the compounds shown in Table 11 were obtained.

TABLE 11

| Reference example | R¹ | R² | R³ | Rᵃ | Melting point |
|---|---|---|---|---|---|
| 69 | 4-F | 2-CN | H | H | 175–176° C. |
| 70 | 4-CN | 2-F | H | H | 168–169° C. |

Reference Example 71

(1) To a mixed solution comprising 1660 ml of 2N sodium carbonate solution, 900 ml of ethanol and 1650 ml of diethoxyethane were added 150 g of 2-chloro-3-nitropyridine, 138 g of phenylboric acid and 54.7 g of tetrakis (triphenylphosphine) palladium (0), and the stirred mixture was further stirred under nitrogen atmosphere for 20 hours under heating. Then, this mixture was cooled, and filtered through Cellite. The filtrate was concentrated, and the concentrated residue was added to ethyl acetate and brine to effect extraction. The organic layer was dried over anhydrous sodium sulfate, and concentrated. The concentrated residue was purified by silica gel column chromatography (hexane/ethyl acetate=5/1) to give 179 g of 3-nitro-2-phenylpyridine.
Oily Product (2) In a mixed solution comprising 1500 ml of ethanol and 96 ml of conc. hydrochloric acid was dissolved 30 g of 3-nitro-2-phenylpyridine obtained in (1), and 9.6 g of platinum oxide was added to the solution, to effect hydrogenation until completion of absorption of hydrogen at 1 atm. (about 3 hours). This mixture was filtered through Cellite, and then the filtrate was concentrated. The concentrated residue was added to methylene chloride and a saturated aqueous ammonia to effect extraction. The organic layer was dried over anhydrous sodium sulfate, and concentrated. The concentrated residue was purified by silica gel column chromatography (methylene chloride/ethanol/aqueous ammonia=200/7/1) to give 8.9 g of cis-2-phenyl-piperidin-3-ylamine.
Oily Product (3) To a mixed solution comprising 4200 ml of ethanol and 634 ml of water heated to 60° C. was added 53.3 g of racemic 2-phenyl-piperidin-3-ylamine and the resulting mixture was stirred. To the solution was added little by little 117 g of (2R,3R)-bis(4-methylbenzoyloxy)succinate over 10 minutes. Then, the solution was stirred at a temperature between 60 and 70° C. for 0.5 hours. The solution was allowed to cool at room temperature overnight. The obtained solid state material was collected and vacuum dried at 70° C. (65.8 g). 65.0 g of this sample was recrystallized from 3340 ml of ethanol and 590 ml of water to give 55.7 g of (2S,3S)-2-phenylpiperidin-3-ylamine (2R,3R)-bis(4-methylbenzoyloxy)-succinate.
m.p.=186–188° C. (dec.)

Reference Examples 72 to 80

(1) In the same manner as in Reference example 71(1), the compounds shown in the following Table 12 were obtained.

TABLE 12

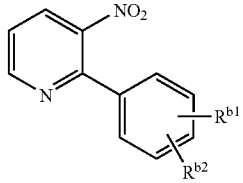

| Reference example | $R^{b1}$ | $R^{b2}$ | Melting point |
| --- | --- | --- | --- |
| 72-(1) | 2-CH₃ | H | Oily product |
| 73-(1) | 3-CH₃ | H | Oily product |
| 74-(1) | 4-CH₃ | H | 63–65° C. |
| 75-(1) | 2-F | H | 47–49° C. |
| 76-(1) | 3-F | H | 68–70° C. |
| 77-(1) | 4-F | H | 101–102° C. |
| 78-(1) | 4-F | 2-F | 100–101° C. |
| 79-(1) | 4-F | 3-F | 86–88° C. |
| 80-(1) | 4-F | 3-CH₃ | 75–77° C. |

(2) In the same manner as in Reference example 71(2), the compounds shown in the following Table 13 were obtained.

TABLE 13

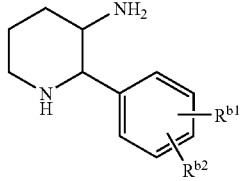

| Reference example | $R^{b1}$ | $R^{b2}$ | Melting point |
| --- | --- | --- | --- |
| 72-(2) | 2-CH₃ | H | Oily product |
| 73-(2) | 3-CH₃ | H | Oily product |
| 74-(2) | 4-CH₃ | H | Oily product |
| 75-(2) | 2-F | H | Oily product |
| 76-(2) | 3-F | H | Oily product |
| 77-(2) | 4-F | H | Oily product |
| 78-(2) | 4-F | 2-F | Oily product |
| 79-(2) | 4-F | 3-F | Oily product |
| 80-(2) | 4-F | 3-CH₃ | Oily product |

(3) In the same manner as in Reference example 71(3), the compounds shown in the following Table 14 were obtained.

TABLE 14

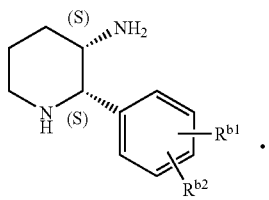

| Reference example | $R^{b1}$ | $R^{b2}$ | Melting point |
| --- | --- | --- | --- |
| 72-(3) | 2-CH₃ | H | 151–153° C. |
| 73-(3) | 3-CH₃ | H | 178–179° C. |
| 74-(3) | 4-CH₃ | H | 173–175° C. |
| 75-(3) | 2-F | H | 137–138° C. |
| 76-(3) | 3-F | H | 185–186° C. |
| 77-(3) | 4-F | H | 190–191° C. |
| 78-(3) | 4-F | 2-F | 131–134° C. |
| 79-(3) | 4-F | 3-F | 187–189° C. |
| 80-(3) | 4-F | 3-CH₃ | 189–190° C. |

Reference Example 81

(1) A mixture of 25.15 g of 4-chlorobenzaldehyde, 26.32 g of methyl-4-nitrobutyrate and 13.79 g of ammonium acetate in 45 ml of acetic acid was refluxed under heating for 4 hours. After cooling to 0° C., precipitated crystals were collected by filtration. To the obtained crystals were added dichloromethane and a saturated aqueous sodium hydrogen carbonate solution to dissolve the crystals. This solution was separated and the organic solvent was removed under reduced pressure. The residue was recrystallized from 100 ml of ethyl acetate and 200 ml of hexane to give 24.65 g of trans-6-(4-chlorophenyl)-5-nitropiperidin-2-one.
m.p.=148–150° C.

(2) In 400 ml of dichloromethane and 400 ml of methanol was dissolved 24.50 g of the compound obtained in (1), and 11.87 g of potassium t-butoxide was added to the solution. The mixture was cooled to –70° C., and ozone was passed through the mixture for 3 hours. The mixture was purged by nitrogen and dimethylsulfide was added to the mixture. Then, the solvent was removed under reduced pressure, and the obtained residue was extracted with dichloromethane. The combined whole organic extracts were washed with brine, dried over anhydrous magnesium sulfate, and the solvent was removed under reduced pressure to give 9.70 g of 6-(4-chlorophenyl)-piperidin-2,5-dione.
MS (M+1) 220

(3) To 114 ml of pyridine was added a mixture comprising 19.01 g of the compound obtained in (2) and 14.77 g of hydroxylamine hydrochloride, and the resulting mixture was stirred under nitrogen atmosphere at room temperature for 15 hours. Then, the solvent was removed under reduced pressure, the crude mixture was distributed between chloroform and 2N aqueous hydrochloric acid, and the aqueous layer was further extracted with chloroform. To the combined whole organic extracts was added a saturated aqueous sodium hydrogen carbonate solution to make the mixture basic. After separating the liquids, the organic extract was washed with brine, and the solvent was removed under reduced pressure. The residue was triturated with ether to give 19.02 g of 6-(4-chlorophenyl)-piperidin-2,5-dione-5-oxime. m.p.=177–180° C. (dec.)

(4) Under nitrogen atmosphere, 240 ml of tetrahydrofuran was added to 14.56 g of zirconium (IV) chloride cooled to 0° C. To the mixture was added 9.46 g of sodium borohydride, and the resulting mixture was warmed to room temperature over 15 minutes while stirring. To the above-mentioned mixture was added dropwise 120 ml of a tetrahydrofuran suspension containing 11.90 g of the compound obtained in (3), and the resulting mixture was stirred at room temperature for 21 hours.

To the above-mentioned mixture was added a mixed solution of 130 ml of methanol and 24 ml of conc. hydrochloric acid, and the resulting mixture was refluxed under heating for 3 hours. The solvent in the mixture was removed. To the residue were added 100 ml of 28% aqueous ammonia and 200 ml of chloroform to suspend the residue, and after removing the insoluble materials by filtration, the filtrate was extracted with chloroform. The extract was dried over anhydrous sodium sulfate, and the solvent was removed to give an oily product.

To the oily product was added 130 g of zinc powder, and the mixture was stirred in 400 ml of the solution comprising 2N hydrochloric acid:water:acetic acid=1:1:1 for 3 days. After removing the zinc powder by filtration, the solvent was removed, and 2N aqueous sodium hydroxide solution was added to the residue to make the mixture basic. To the mixture was added dichloromethane and insoluble materials were removed by filtration. The filtrate was separated, and further the aqueous layer was extracted with dichloromethane. The combined whole organic extracts were dried over anhydrous sodium sulfate, and the solvent was removed to give 3.87 g of 2-(4-chlorophenyl)-piperidin-3-ylamine as an oily product (cis, trans mixture).

(5) To 120 ml of dichloromethane was added a mixture comprising 3.87 g of the compound obtained in (4), 16.4 g of di-t-butyldicarbonate and 10.1 g of triethylamine, and the resulting mixture was stirred under nitrogen atmosphere at room temperature for 14 hours. To the reaction mixture was added water, and after separating the liquids, the organic extract was dried over anhydrous sodium sulfate and the solvent was removed. The residue was purified by silica gel column chromatography (n-hexane/ethyl acetate=4/1), to separate a cis-isomer and a trans-isomer. To the obtained cis-isomer was added 4N hydrochloric acid/dioxane, and after stirring the mixture at room temperature for one hour, the solvent was removed under reduced pressure. To the residue was added 4N aqueous sodium hydroxide solution to make the mixture basic, and the resulting mixture was extracted with chloroform. The combined whole organic extracts were dried over anhydrous sodium sulfate, and the solvent was removed to give 690 mg of cis-2-(4-chlorophenyl)-piperidin-3-ylamine as an oily product.

(6) In 56 ml of ethanol and 9 ml of water heated to 60° C. was dissolved 690 mg of racemic 2-(4-chlorophenyl)piperidin-3-ylamine, and 1.30 g of (2R,3R)-bis(4-methylbenzoyloxy)succinate was added to the solution. The solution was stirred at a temperature between 60 and 70° C. for 0.5 hours, and allowed to cool overnight. After collecting the precipitated crystals by filtration, the crystals were washed with ethanol, and dried at 70° C. under reduced pressure. Subsequently, the crystals were recrystallized from 56 ml of ethanol and 10 ml of water to give 677 mg of (2S,3S)-2-(4-chlorophenyl)piperidin-3-ylamine-(2R,3R)-bis(4-methylbenzoyloxy)succinate. m.p.=201–203° C.

Reference Examples 82 to 85

In the same manner as in Reference example 81, the following compounds in Table 15 were obtained.

TABLE 15

| Reference example | $R^{b1}$ | $R^{b2}$ | Melting point |
|---|---|---|---|
| 82 | 2-Cl | H | 132–135° C. |
| 83 | 3-Cl | H | 189–191° C. |
| 84 | 4-CF$_3$ | H | 208–210° C. |
| 85 | 4-OCH$_3$ | H | 143–146° C. |

Reference Example 86

In 70 ml of toluene were suspended 320 mg of 2-methoxy-5-bromobenzaldehyde, 570 mg of 2-trifluoromethylphenylboric acid, 45 mg of palladium acetate and 136 mg of tri-o-tollylphosphine under nitrogen atmosphere, and then, 3.3 ml of 2M aqueous sodium carbonate solution was added to the suspension, and a small amount of ethanol was further added thereto. The obtained solution was heated up to 70° C., and stirred for 16 hours. The reaction mixture was cooled to room temperature, and the formed black precipitates were removed by filtration. The filtrate was washed with an aqueous sodium bicarbonate solution and brine, dried over anhydrous magnesium sulfate, and concentrated under reduced pressure. The concentrated residue was purified by silica gel column chromatography (n-hexane/ethyl acetate=10/1) and crystallized from diisopropyl ether and n-hexane to give 298 mg of 2-methoxy-5-(2-trifluoromethylphenyl)benzaldehyde.
Oily Product

UTILIZABILITY IN INDUSTRY

The compounds or a salt thereof of the present invention have an excellent tachykinin receptor antagonistic action.

Also, the compounds of the present invention are excellent in terms of absorption, transportability into brain, sustainability and metabolic stability, so that they have excellent pharmaceutical effects.

What is claimed is:

1. A 5-phenylbenzylamine compound represented by the formula [1-a]:

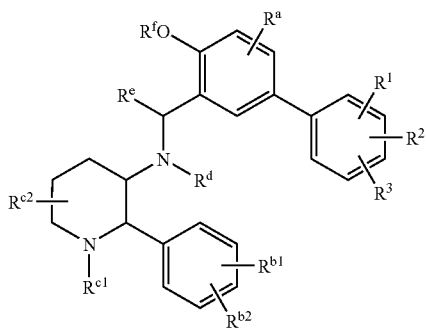

[1-a]

wherein $R^1$ represents a halogen atom, a lower alkyl group, a halogeno-lower alkyl group, a lower alkoxy group, a hydroxy-lower alkyl group, a lower alkoxy-lower alkyl group, an amino group optionally substituted by a lower alkyl group, phenyl group, naphthyl group, nitro group, cyano group, —CO—NH-lower alkyl, —CO—N(lower alkyl)$_2$, —NH—CO-lower alkyl, or —COO-lower alkyl, $R^2$ represents a hydrogen atom, a halogen atom, a lower alkyl group, a halogeno-lower alkyl group, a lower alkoxy group, or cyano group, $R^3$ represents a hydrogen atom, a halogen atom, a lower alkyl group, a halogeno-lower alkyl group, a lower alkoxy group, or cyano group, $R^a$ represents a hydrogen atom, a halogen atom, a lower alkyl group, a halogeno-lower alkyl group, or a lower alkoxy group, $R^{b1}$ represents a hydrogen atom, a halogen atom, a lower alkyl group, a halogeno-lower alkyl group, or a lower alkoxy group, $R^{b2}$ represents a hydrogen atom, a halogen atom, a lower alkyl group, a halogeno-lower alkyl group, or a lower alkoxy group, $R^{c1}$ represents a hydrogen atom, a lower alkyl group, or an acyl group, $R^{c2}$ represents a hydrogen atom or a lower alkyl group, $R^d$ represents a hydrogen atom, a lower alkyl group or an acyl group, $R^e$ represents a hydrogen atom or a lower alkyl group, and $R^f$ represents a lower alkyl group or a cyclic lower alkyl group, or a pharmaceutically acceptable salt thereof.

2. The compound according to claim 1, wherein $R^a$ is hydrogen atom or a lower alkoxy group, $R^{b1}$ is hydrogen atom or a halogen atom, $R^{b2}$ is hydrogen atom, $R^{c1}$ is hydrogen atom, $R^{c2}$ is hydrogen atom or methyl group, $R^d$ is hydrogen atom, $R^e$ is hydrogen atom, and $R^f$ is methyl group.

3. The compound according to claim 2, wherein $R^1$ is a halogen atom, a lower alkyl group, nitro group or cyano group, $R^2$ is hydrogen atom or a halogen atom, and $R^3$ is hydrogen atom or a halogen atom.

4. The compound according to claim 2, wherein $R^1$ is a halogen atom or cyano group, $R^2$ is hydrogen atom or a halogen atom, and $R^3$ is hydrogen atom or a halogen atom.

5. The compound according to claim 3, wherein $R^1$ is a substituent at 4-position.

6. The compound according to claim 1, wherein $R^1$ is a halogen atom or cyano group, $R^2$ is hydrogen atom or a halogen atom, $R^3$, $R^a$, $R^{b1}$, $R^{b2}$, $R^{c1}$, $R^d$ and $R^e$ are hydrogen atoms, $R^{c2}$ is hydrogen atom or methyl group, $R^f$ is methyl group, and $R^1$ is a substituent at 4-position.

7. A compound selected from the following (A) to (F):
(A) [2-methoxy-5-(4-fluorophenyl)benzyl][(2S,3S)-2-phenylpiperidin-3-yl]amine
(B) [2-methoxy-5-(4-chlorophenyl)benzyl][(2S,3S)-2-phenylpiperidin-3-yl]amine
(C) [2-methoxy-5-(4-cyanophenyl)benzyl][(2S,3S)-2-phenylpiperidin-3-yl]amine
(D) [2-methoxy-5-(2-fluoro-4-cyanophenyl)benzyl][(2S,3S)-2-phenylpiperidin-3-yl]amine
(E) [2-methoxy-5-(4-cyanophenyl)benzyl][(2S,3S,6R)-6-methyl-2-phenylpiperidin-3-yl]amine, and
(F) [2-methoxy-5-(2-fluoro-4-cyanophenyl)benzyl][(2S,3S,6R)-6-methyl-2-phenylpiperidin-3-yl]amine or a pharmaceutically acceptable salt thereof.

8. A process for preparing a 5-phenylbenzylamine compound represented by the formula [1-a]:

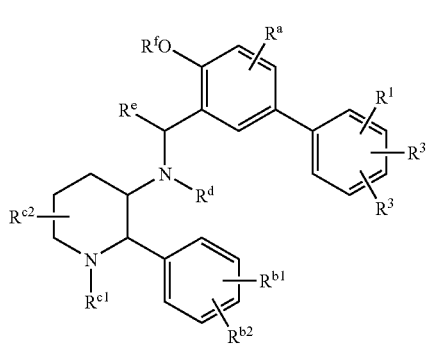

[1-a]

wherein $R^1$ represents a halogen atom, a lower alkyl group, a halogeno-lower alkyl group, a lower alkoxy group, a hydroxy-lower alkyl group, a lower alkoxy-lower alkyl group, an amino group optionally substituted by a lower alkyl group, phenyl group, naphthyl group, nitro group, cyano group, —CO—NH-lower alkyl, —CO—N(lower alkyl)$_2$, —NH—CO-lower alkyl, or —COO-lower alkyl, $R^2$ represents a hydrogen atom, a halogen atom, a lower alkyl group, a halogeno-lower alkyl group, a lower alkoxy group, or cyano group, $R^3$ represents a hydrogen atom, a halogen atom, a lower alkyl group, a halogeno-lower alkyl group, a lower alkoxy group, or cyano group, $R^a$ represents a hydrogen atom, a halogen atom, a lower alkyl group, a halogeno-lower alkyl group, or a lower alkoxy group, $R^{b1}$ represents a hydrogen atom, a halogen atom, a lower alkyl group, a halogeno-lower alkyl group, or a lower alkoxy group, $R^{b2}$ represents a hydrogen atom, a halogen atom, a lower alkyl group, a halogeno-lower alkyl group, or a lower alkoxy group, $R^{c1}$ represents a hydrogen atom, a lower alkyl group, or an acyl group, $R^{c2}$ represents a hydrogen atom, or a lower alkyl group, $R^d$ represents a hydrogen atom, a lower alkyl group, or an acyl group, $R^e$ represents a hydrogen atom or a lower alkyl group, $R^f$ represents a lower alkyl group or a cyclic lower alkyl group, said process comprising:

subjecting a compound represented by the formula [2-a]:

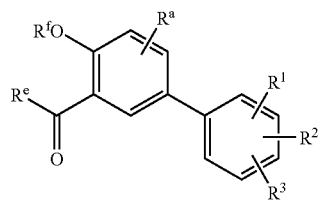

[2-a]

wherein $R^1$, $R^2$, $R^3$, $R^a$, $R^e$ and $R^f$ have the same meanings as defined above, and a compound represented by the formula [3]:

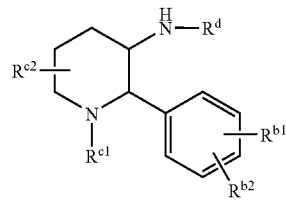

[3]

wherein $R^{b1}$, $R^{b2}$, $R^{c1}$, $R^{c2}$ and $R^d$ have the same meanings as defined above, to a reductive condensation reaction, and making the product a pharmaceutically acceptable salt, if desired.

9. a pharmaceutical composition comprising the compound according to claim 1 in an effective dose for treatment and a pharmaceutically acceptable carrier.

10. A method of treating emesis which comprises administering the compound according to claim 1 in an effective dose for the treatment to a mammal.

* * * * *